(12) United States Patent
Baum et al.

(10) Patent No.: US 9,997,362 B2
(45) Date of Patent: Jun. 12, 2018

(54) COBALT CVD

(71) Applicant: ENTEGRIS, INC., Billerica, MA (US)

(72) Inventors: Thomas H. Baum, New Fairfield, CT (US); Scott L. Battle, Cedar Park, TX (US); David W. Peters, Kingsland, TX (US); Philip S. H. Chen, Bethel, CT (US)

(73) Assignee: Entegris, Inc., Billerica, MA (US)

(*) Notice: Subject to any disclaimer, the term of this patent is extended or adjusted under 35 U.S.C. 154(b) by 0 days. days.

(21) Appl. No.: 15/302,741

(22) PCT Filed: Mar. 26, 2015

(86) PCT No.: PCT/US2015/022597
§ 371 (c)(1),
(2) Date: Oct. 7, 2016

(87) PCT Pub. No.: WO2015/157004
PCT Pub. Date: Oct. 15, 2015

(65) Prior Publication Data
US 2017/0032973 A1    Feb. 2, 2017

Related U.S. Application Data

(60) Provisional application No. 61/975,994, filed on Apr. 7, 2014.

(51) Int. Cl.
*H01L 21/44* (2006.01)
*H01L 21/285* (2006.01)
(Continued)

(52) U.S. Cl.
CPC ........ *H01L 21/28562* (2013.01); *C07F 15/06* (2013.01); *C23C 16/06* (2013.01);
(Continued)

(58) Field of Classification Search
CPC ................ C23C 16/16; C23C 16/4481; H01L 21/02697; H01L 21/28506; H01L 21/28556
See application file for complete search history.

(56) References Cited

U.S. PATENT DOCUMENTS 8,524,600 B2    9/2013  Lei et al.
2005/0014365 A1   1/2005  Moon et al.
(Continued)

FOREIGN PATENT DOCUMENTS

KR  10-2008-0110897 A   12/2008

*Primary Examiner* — Selim Ahmed
*Assistant Examiner* — Evan Clinton

(57) ABSTRACT

A cobalt deposition process, including: volatilizing a cobalt precursor selected from among CCTBA, CCTMSA, and CCBTMSA, to form a precursor vapor; and contacting the precursor vapor with a substrate under vapor deposition conditions effective for depositing on the substrate (i) high purity, low resistivity cobalt or (ii) cobalt that is annealable by thermal annealing to form high purity, low resistivity cobalt. Such cobalt deposition process can be used to manufacture product articles in which the deposited cobalt forms an electrode, capping layer, encapsulating layer, diffusion layer, or seed for electroplating of metal thereon, e.g., a semiconductor device, flat-panel display, or solar panel.

14 Claims, 18 Drawing Sheets

(51) Int. Cl.
  *C07F 15/06* (2006.01)
  *C23C 16/18* (2006.01)
  *C23C 16/56* (2006.01)
  *H01L 21/768* (2006.01)
  *C23C 16/06* (2006.01)
  *C23C 16/455* (2006.01)
  *H01L 21/321* (2006.01)
  *H01L 23/532* (2006.01)

(52) U.S. Cl.
  CPC ............ *C23C 16/18* (2013.01); *C23C 16/455* (2013.01); *C23C 16/56* (2013.01); *H01L 21/28556* (2013.01); *H01L 21/28568* (2013.01); *H01L 21/321* (2013.01); *H01L 21/76843* (2013.01); *H01L 21/76849* (2013.01); *H01L 21/76864* (2013.01); *H01L 21/76873* (2013.01); *H01L 23/53257* (2013.01); *H01L 2924/0002* (2013.01)

(56) References Cited

U.S. PATENT DOCUMENTS

| | | | |
|---|---|---|---|
| 2009/0208637 A1* | 8/2009 | Chen | C07F 15/06 |
| | | | 427/78 |
| 2011/0124192 A1 | 5/2011 | Ganguli et al. | |
| 2012/0252207 A1* | 10/2012 | Lei | H01L 21/76885 |
| | | | 438/653 |
| 2013/0260555 A1 | 10/2013 | Zope et al. | |
| 2015/0093891 A1* | 4/2015 | Zope | H01L 21/76877 |
| | | | 438/618 |

* cited by examiner

COBALT CVD

CROSS-REFERENCE TO RELATED APPLICATIONS

This application claims the benefit from International Application No. PCT/US2015/022597, filed Mar. 26, 2015, which in turn claims the benefit of priority under 35 USC 119 of U.S. Provisional Patent Application No. 61/975,994 filed Apr. 7, 2014 in the names of Thomas H. Baum, et al. for "COBALT CVD", both of which are incorporated herein by reference in their entireties for all purposes.

The benefit of priority under 35 USC 119 of U.S. Provisional Patent Application No. 61/975,994 filed Apr. 7, 2014 in the names of Thomas H. Baum, et al. for "COBALT CVD" is hereby claimed. The disclosure of U.S. Provisional Patent Application No. 61/975,994 is hereby incorporated herein by reference, in its entirety, for all purposes.

FIELD

The present disclosure relates to high purity, low resistivity (<50 µΩ-cm) cobalt and products comprising same, and to precursors and processes for forming such high purity, low resistivity cobalt on substrates, e.g., in the manufacture of semiconductor products, flat-panel displays, and solar panels.

DESCRIPTION OF THE RELATED ART

Cobalt is finding increasing use in semiconductor manufacturing, such as in fabrication of integrated circuits in which cobalt disilicide has been progressively displacing titanium silicide as feature and linewidth dimensions decrease, since it does not entail the linewidth dependent sheet resistance issues that are characteristic of titanium silicide. Cobalt also is currently under consideration as a conductive cap over copper lines or as part of the barrier/adhesion layer liner for copper lines and contacts, as an encapsulant material, as a seed material for electroless and electroplating processes, and as a replacement material for copper in wiring and interconnects of integrated circuits. Cobalt additionally has elicited interest as a result of its magnetic properties for data storage applications and its potential for spintronics applications.

Interconnects are critical components of integrated circuitry, providing power/ground connections and distribution of clock and other signals. Local interconnects comprise the lines that connect gates and transistors, intermediate interconnects provide wiring within functional blocks of integrated circuitry, and global interconnects distribute clock and other signals and provide power/ground connections for the entire integrated circuit. Interconnects increasingly are a dominant factor in determining system performance and power dissipation of integrated circuits.

In the manufacture of integrated circuitry devices in which copper is used as a metallization material, cobalt liners and back end of the line (BEOL) interconnect caps have been developed for protection of copper interconnects. Recently, it has been proposed to replace the copper interconnect due to problems associated with electron migration. Although various cobalt precursors have been applied to such interconnect fabrication, the deposited cobalt thin films have been plagued by the presence of excess residual carbon and oxygen impurities, which in turn has caused such thin films to exhibit relatively low conductivity (resistivity>50 microohm-cm).

There is accordingly a compelling need in the art for high purity, low resistivity cobalt films and other cobalt structures, for forming interconnects and other metallization features of integrated circuits and other products, e.g., for use as seed material, encapsulants, electroless and electroplating materials, etc., and for processes that enable the deposition of high purity, low resistivity cobalt thin films and structures for such purposes.

SUMMARY

The present disclosure relates to deposition of high purity, low resistivity cobalt on substrates, cobalt precursors useful in such deposition, and product articles comprising high purity, low resistivity cobalt.

In one aspect, the present disclosure relates to a cobalt deposition process, comprising:
volatilizing a cobalt precursor selected from among CCTBA, CCTMSA, and CCBTMSA, to form a precursor vapor; and
contacting the precursor vapor with a substrate under vapor deposition conditions effective for depositing on the substrate (i) high purity, low resistivity cobalt or (ii) cobalt that is annealable by thermal annealing to form high purity, low resistivity cobalt.

In another aspect, the disclosure relates to an article comprising high purity, low resistivity deposited cobalt, as formed by a method comprising a process of the present disclosure.

Other aspects, features and embodiments of the disclosure will be more fully apparent from the ensuing description and appended claims.

Figure 15:
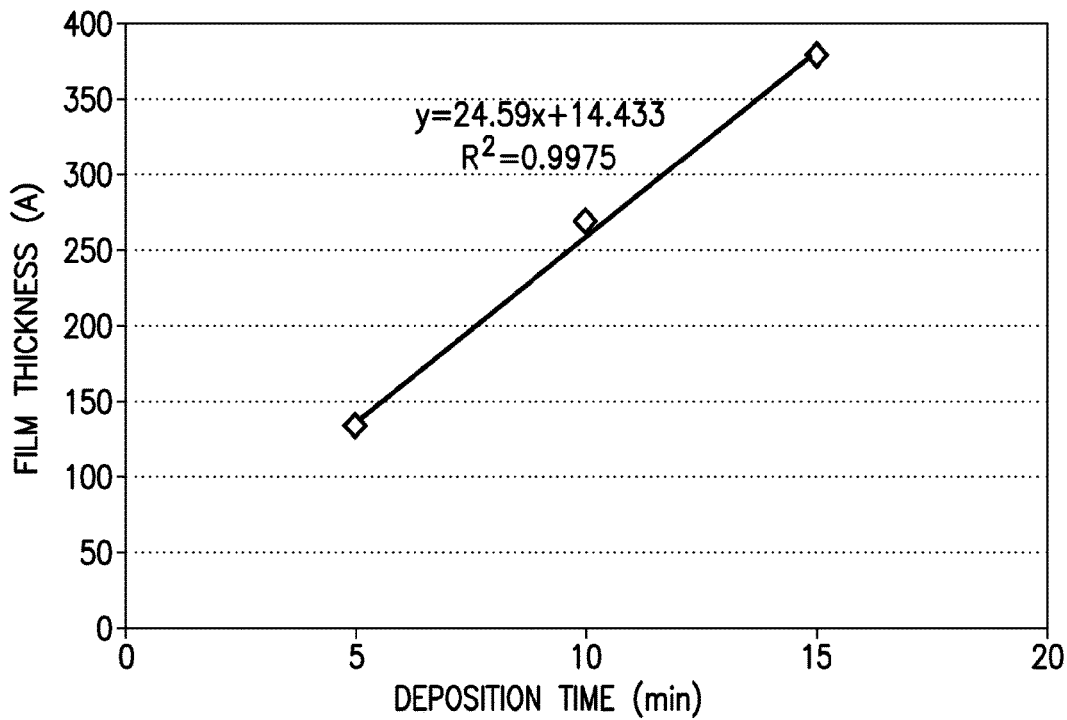
Figure 16:
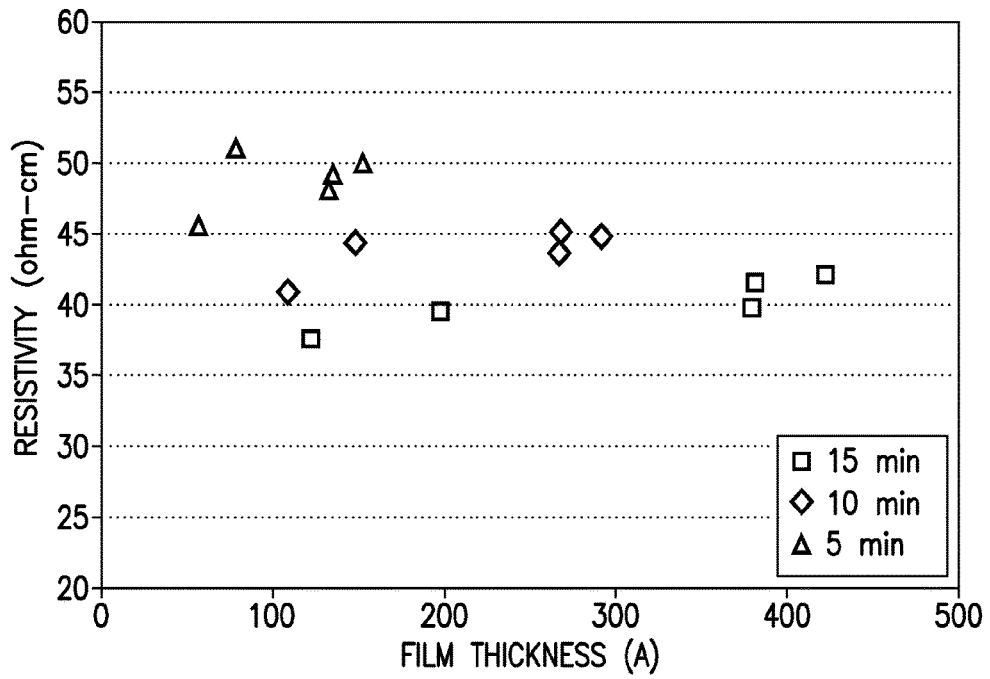

The effects of deposition time on film thickness and resistivity are shown in FIGS. 15 and 16, for deposition of cobalt films at a precursor delivery rate of 100 μmoles/minute.

FIG. 15 is a graph of film thickness, in Angstroms, as a function of deposition time, in minutes, showing the linear relationship between such variables, for cobalt films deposited at a precursor delivery rate of 100 μmoles/minute.

FIG. 16 is a graph of resistivity, in μΩ-cm, as a function of film thickness, in Angstroms, for cobalt films deposited at a delivery rate of 100 μmoles/minute, at deposition times of 5 minutes, 10 minutes, and 15 minutes.

Figure 17:
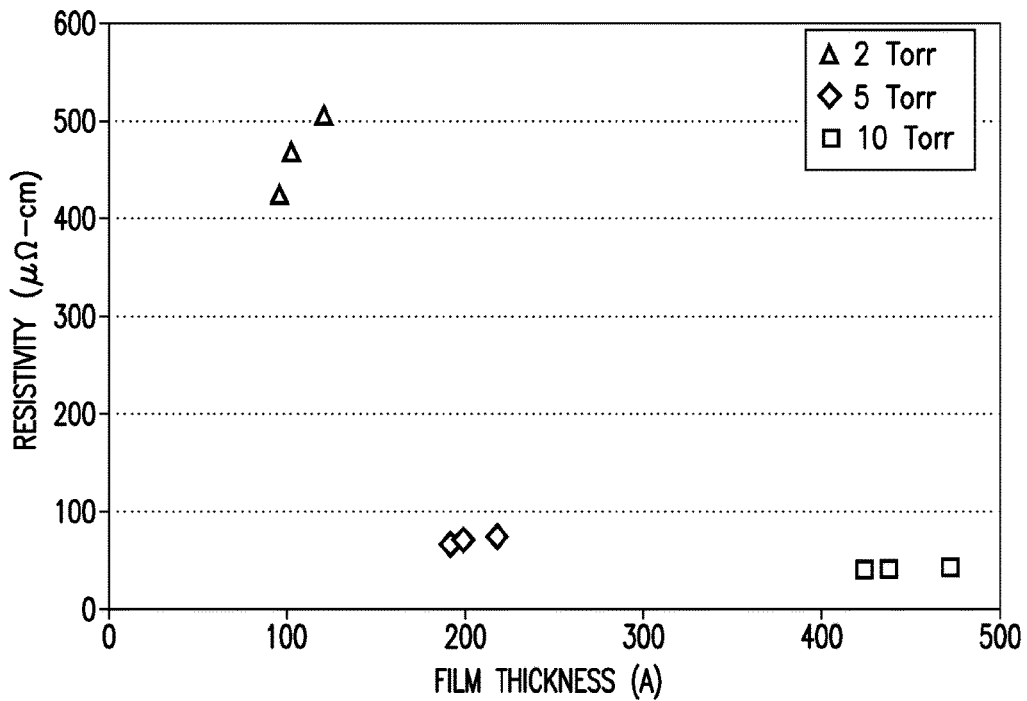

FIG. 17 is a graph of resistivity, in μΩ-cm, as a function of film thickness, in Angstroms, for cobalt films deposited from CCTBA at a delivery rate of 100 μmoles/minute, and a deposition time of 15 minutes, at pressures of 2, 5, and 10 torr.

Figure 18:
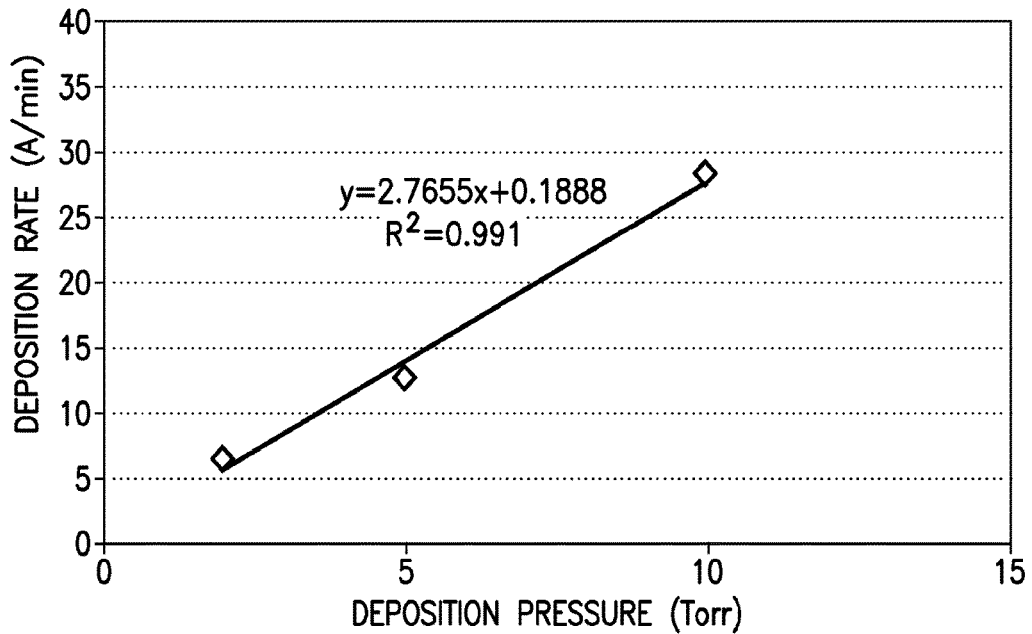

FIG. 18 is a graph of deposition rate, in Angstroms per minute, as a function of deposition pressure, in torr, for cobalt films deposited from CCTBA at a delivery rate of 100 μmoles/minute, and a temperature 150° C.

Figure 19:
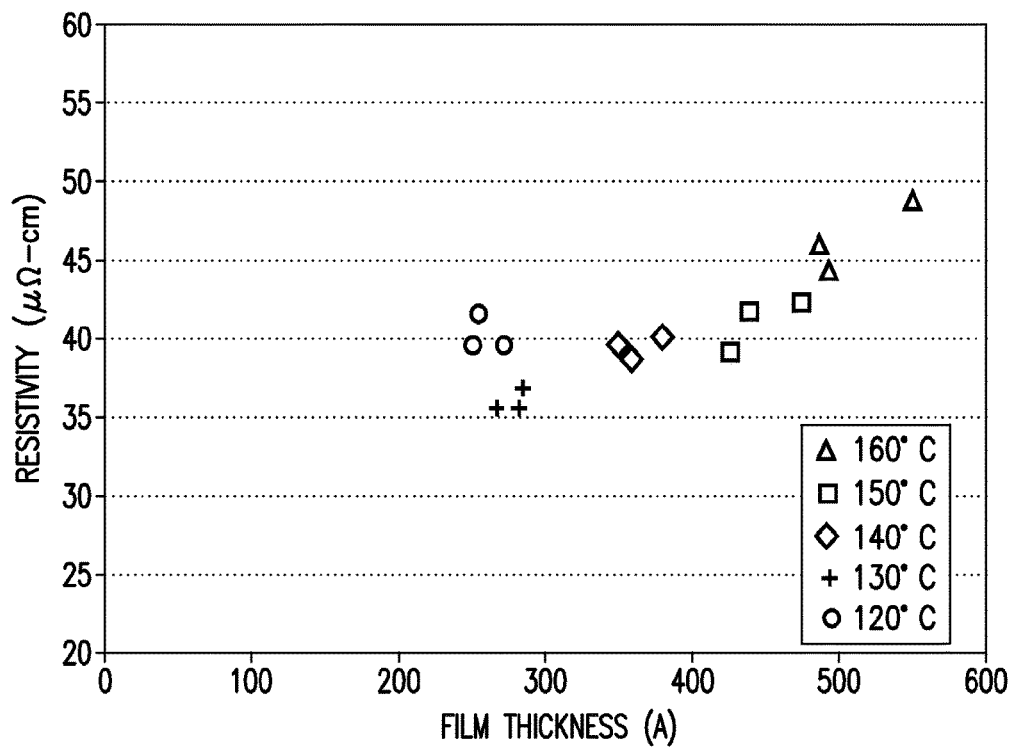

FIG. 19 is a graph of resistivity, in μΩ-cm, as a function of film thickness, in Angstroms, for cobalt films deposited from CCTBA at a delivery rate of 100 μmoles/minute, and a deposition time of 15 minutes, at temperatures of 120° C., 130° C., 140° C., 150° C., and 160° C.

Figure 20:
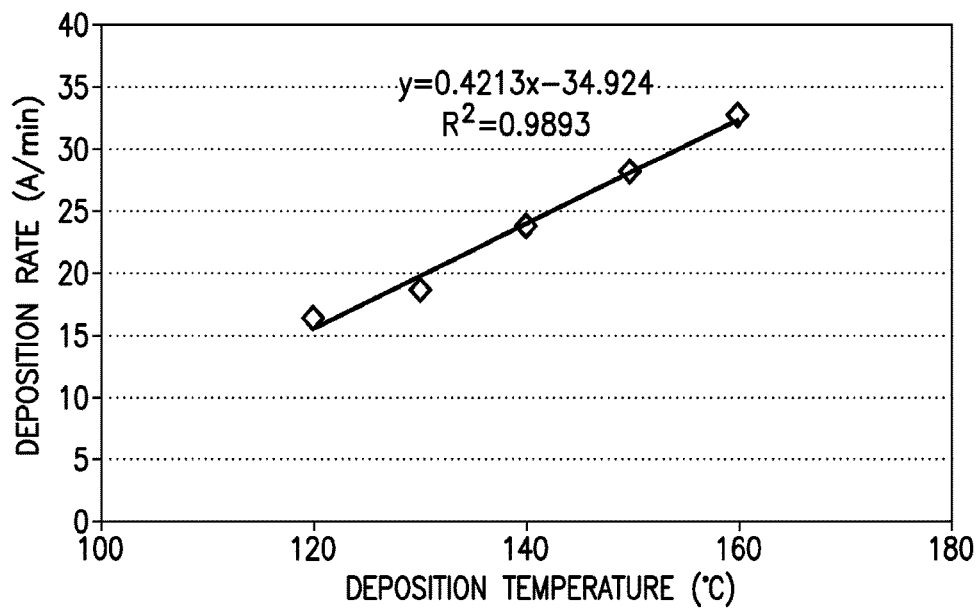

FIG. 20 is a graph of deposition rate, in Angstroms per minute, as a function of deposition temperature, in degrees Centigrade, for cobalt films deposited from CCTBA at a delivery rate of 100 μmoles/minute, and a pressure of 10 torr.

Figure 21:
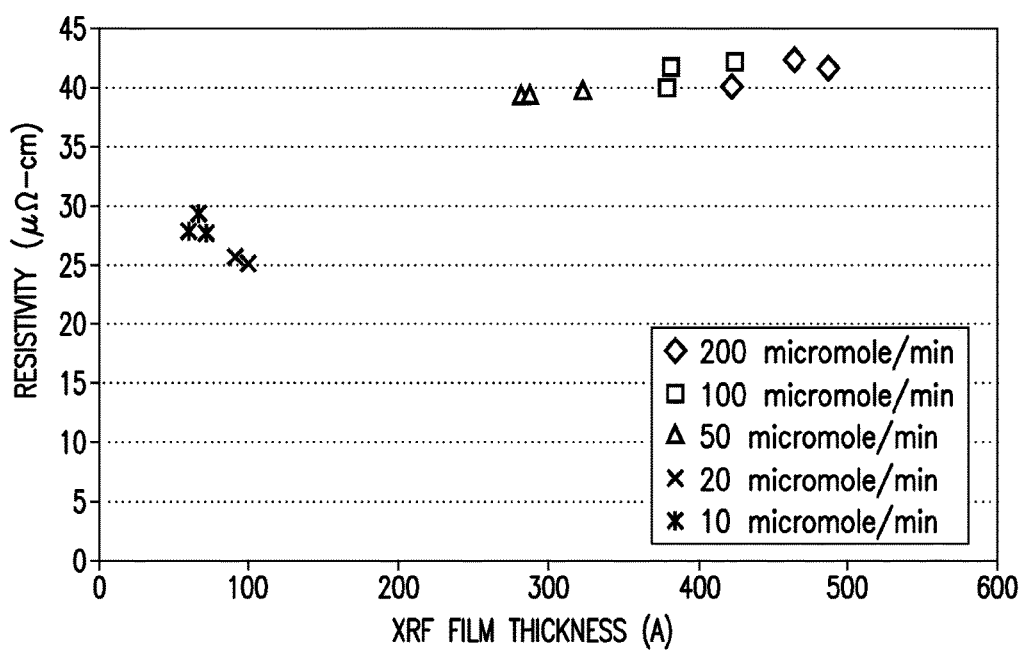

FIG. 21 is a graph of resistivity, in μΩ-cm, as a function of film thickness, in Angstroms, for cobalt films deposited from CCTBA at a temperature of 150° C., pressure of 10 torr, and deposition period of 15 minutes, for precursor delivery rates of 10, 20, 50, 100, and 200 μmoles/minute.

Figure 22:
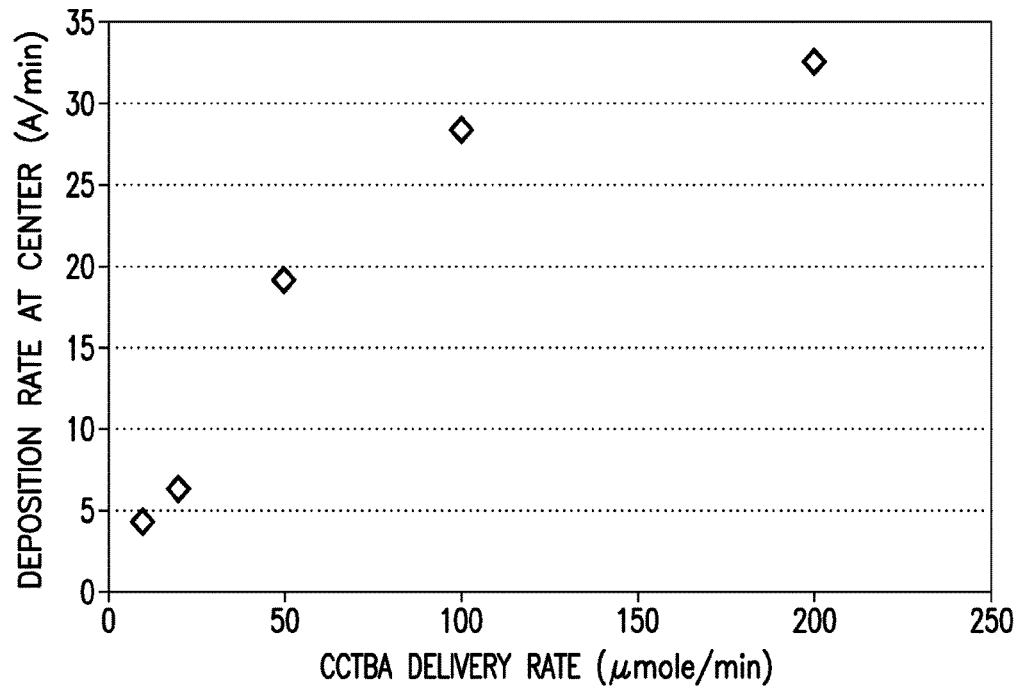

FIG. 22 is a graph of deposition rate, measured at the center of the substrate, in Angstroms per minute, as a function of CCTBA delivery rate, in μmoles/minute, at temperature of 150° C. and a pressure of 10 torr.

Figure 23:
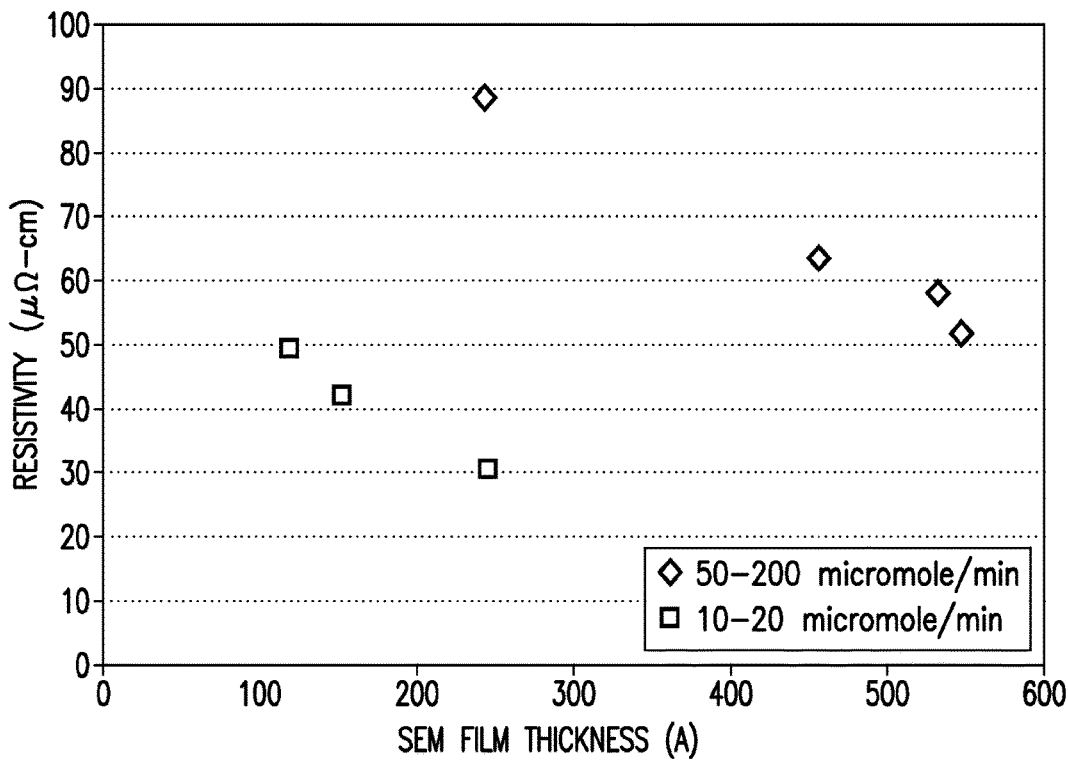

FIG. 23 is a graph of resistivity, in μΩ-cm, as a function of SEM film thickness, in Angstroms, for cobalt films deposited from CCTBA precursor vapor, at temperature of 150° C., and pressure of 10 torr, at precursor delivery rate of 10-20 μmoles/minute (■) and at precursor delivery rate of 50-200 μmoles/minute (♦).

Figure 24:
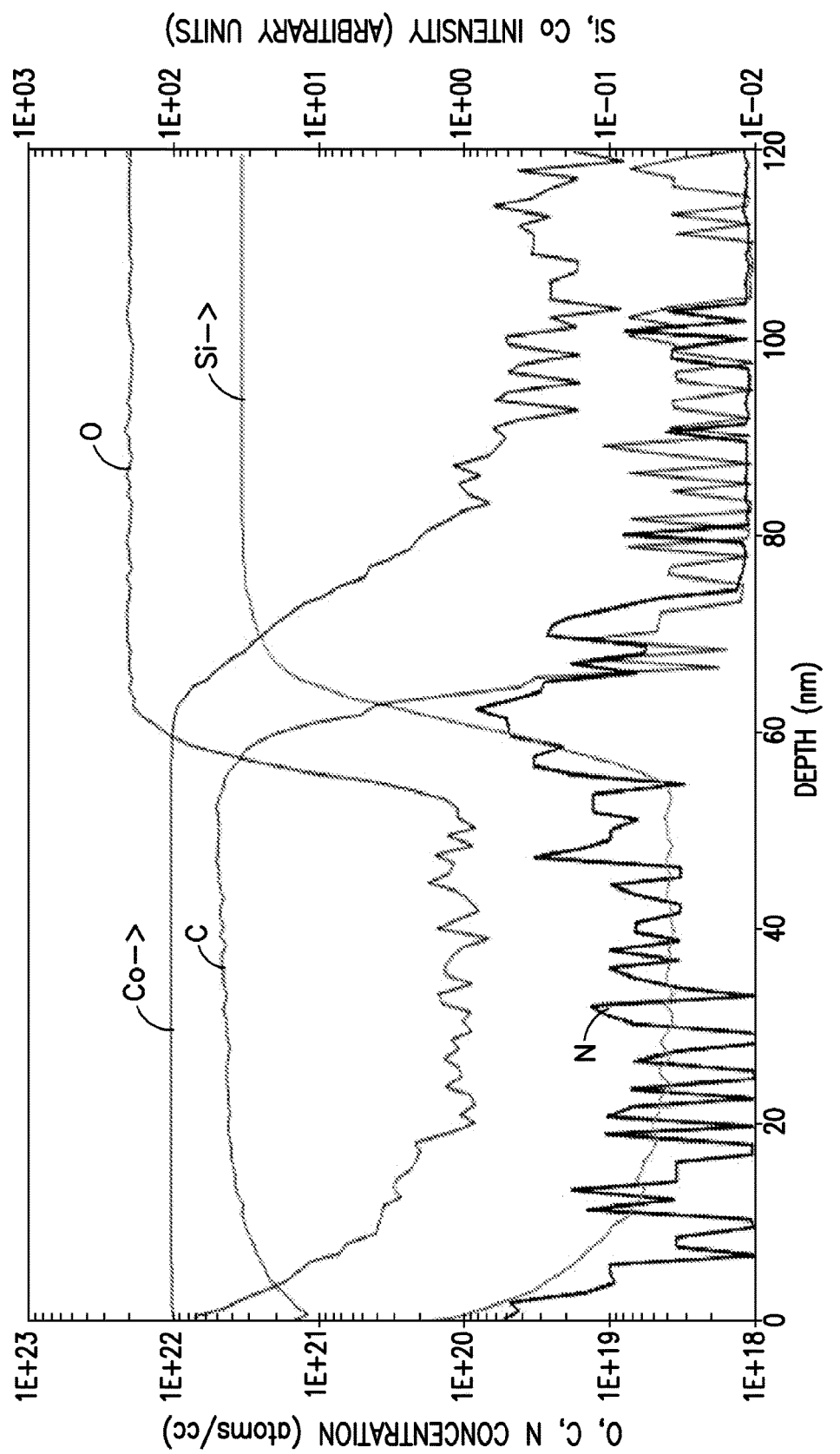

FIG. 24 is a SIMS plot, with concentrations of Si, Co, O, C, and N being shown, in atoms/cc, as a function of depth, in nanometers, for a cobalt film formed by vapor deposition using CCTBA as a precursor, at a precursor flow rate of 200 μmoles/minute, in which the film contained ~4.75 at % carbon and ~0.15 at % oxygen.

Figure 25:
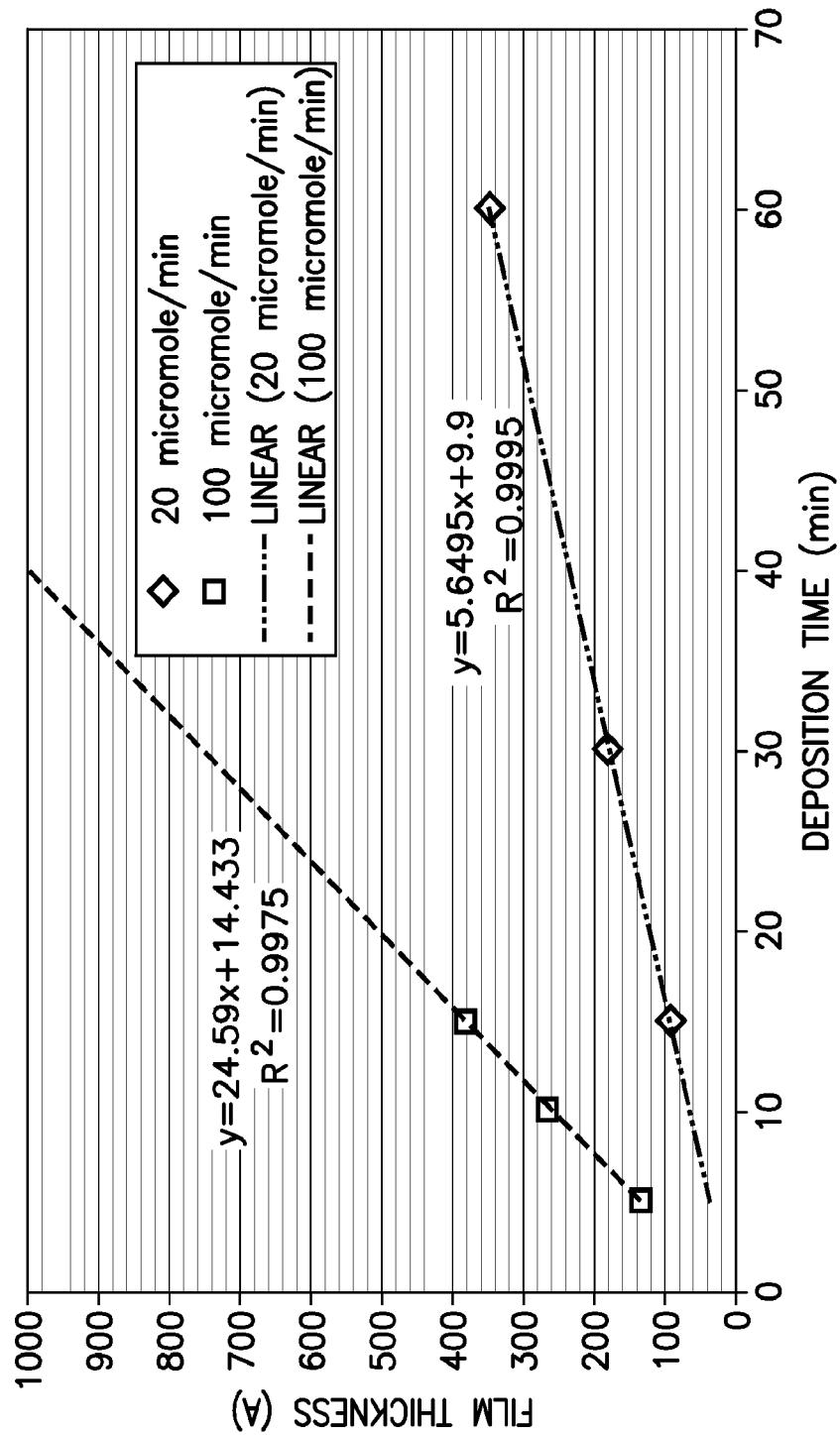

FIG. 25 is a graph of cobalt film thickness, in Angstroms, as a function of deposition time, in minutes, for MOCVD formation of cobalt films using CCTBA precursor to form cobalt films, with precursor delivery rates of 20 and 100 μmoles/minute, at a delivery temperature of 150° C. and 10 Torr pressure.

Figure 26:
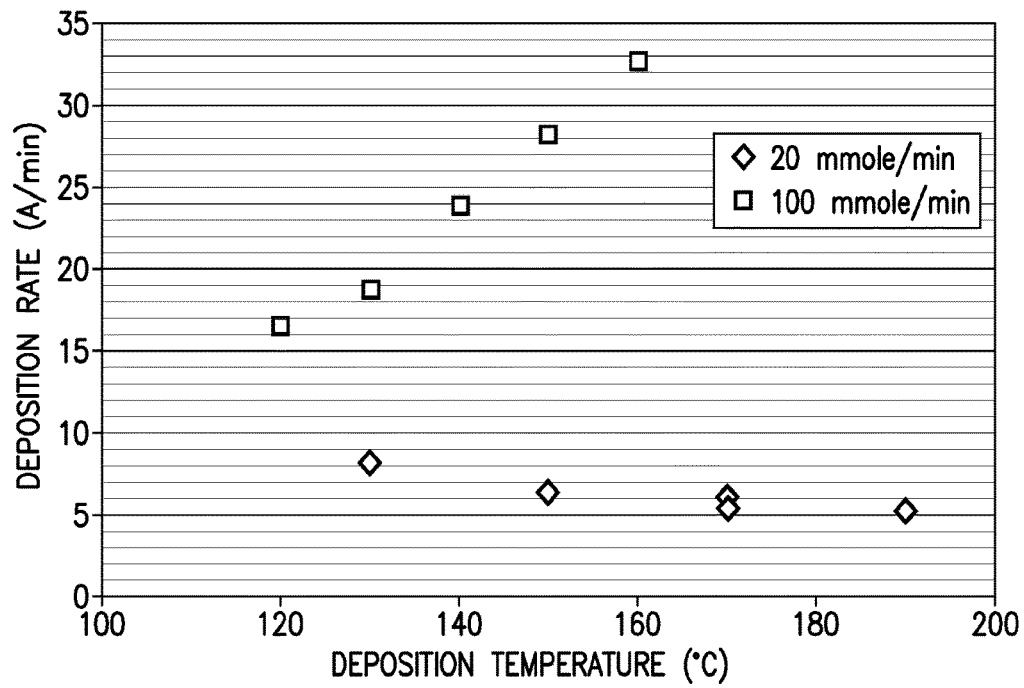

FIG. 26 is a graph of deposition rate, in Angstroms/minute, as a function of deposition temperature, in degrees Centigrade, for cobalt films deposited from CCTBA, delivered at a precursor supply rate of 20 and 100 μmoles/minute, at pressure of 10 torr.

Figure 27:
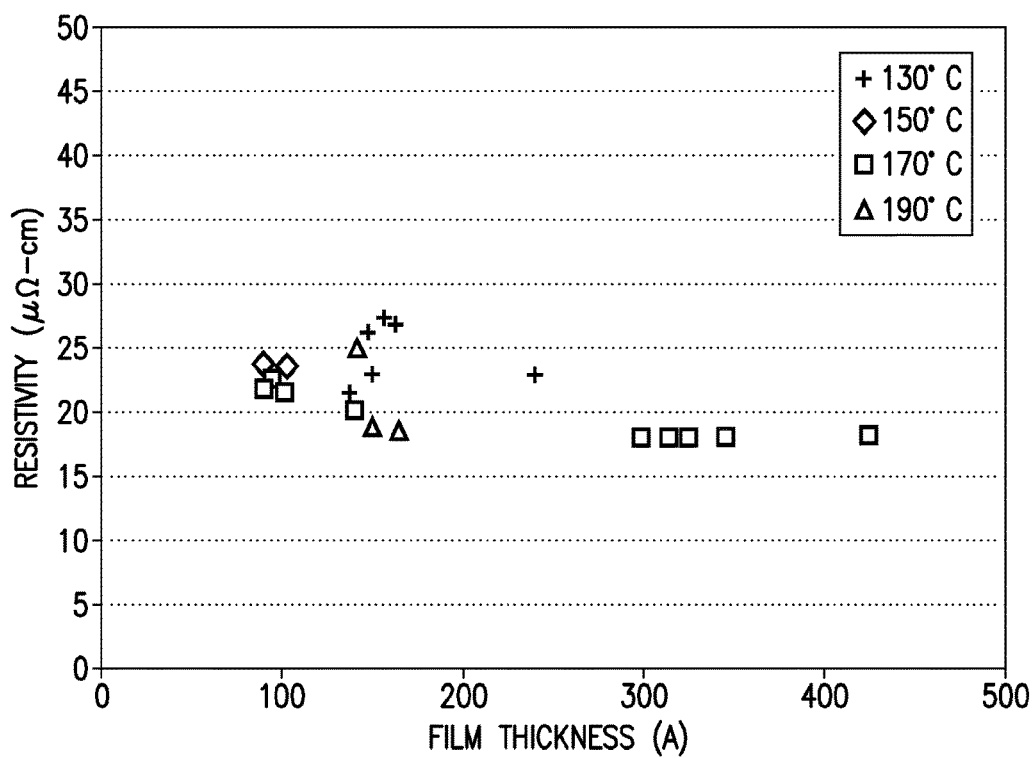

FIG. 27 is a graph of resistivity values, in μΩ-cm, as a function of film thickness, in Angstroms, for cobalt films formed from CCTBA at precursor delivery rate of 20 moles/minute, at 130° C., 150° C., 170° C., and 190° C.

Figure 28:
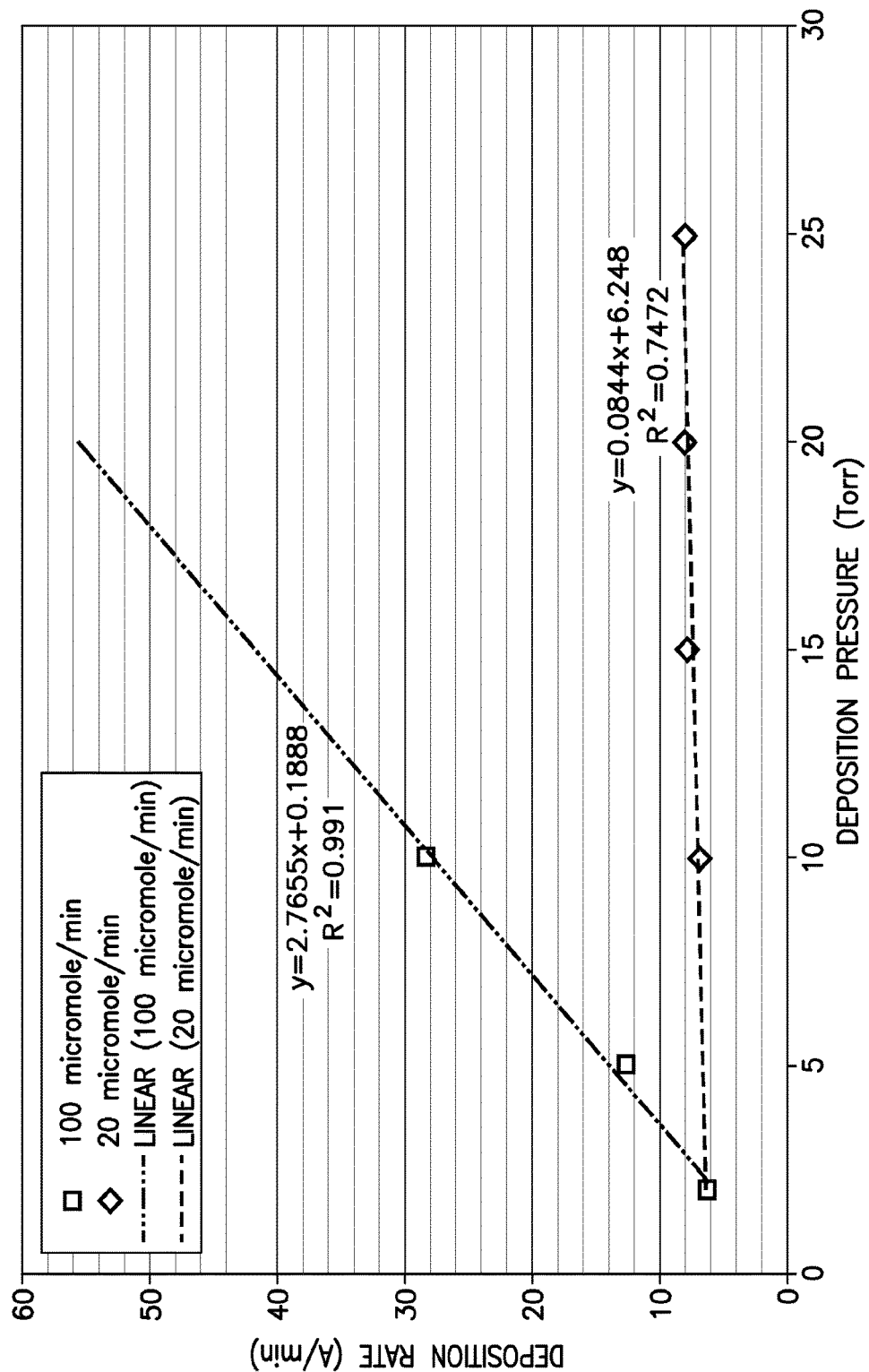

FIG. 28 is a graph of deposition rate, in Angstroms/minute, as a function of deposition pressure, in Torr, for deposition of cobalt films from CCTBA, delivered at a precursor supply rate of 20 μmoles/minute, showing the linear deposition rate/deposition pressure relationship at 20 μmoles/minute, and for comparison, at 100 μmoles/minute.

Figure 29:
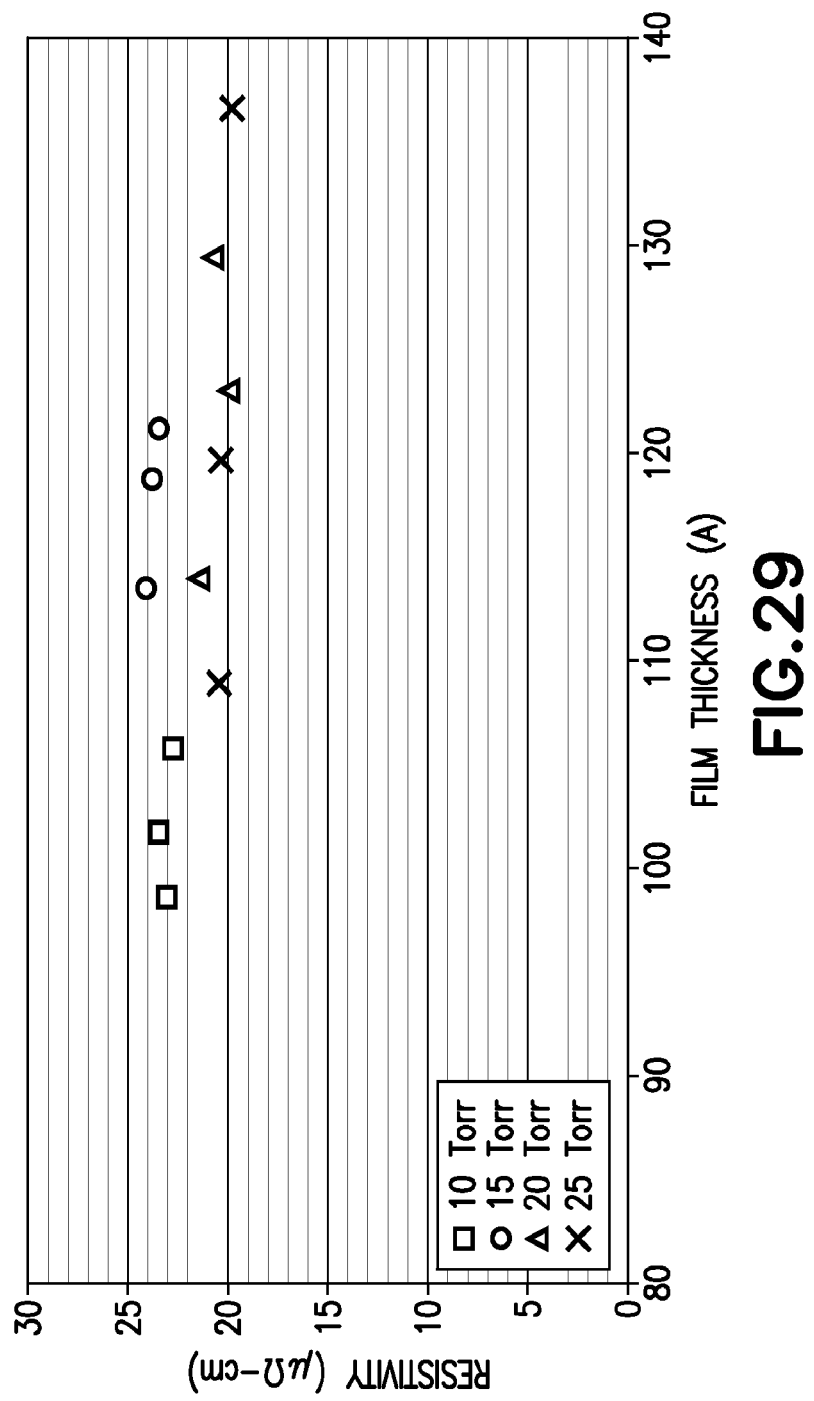

FIG. 29 is a graph of resistivity, in μΩ-cm, as a function of film thickness, in Angstroms, for deposition of cobalt films from CCTBA, delivered at a precursor supply rate of 20 μmoles/minute for 15 minutes, at pressures of 10, 15, 20 and 25 torr.

Figure 30:
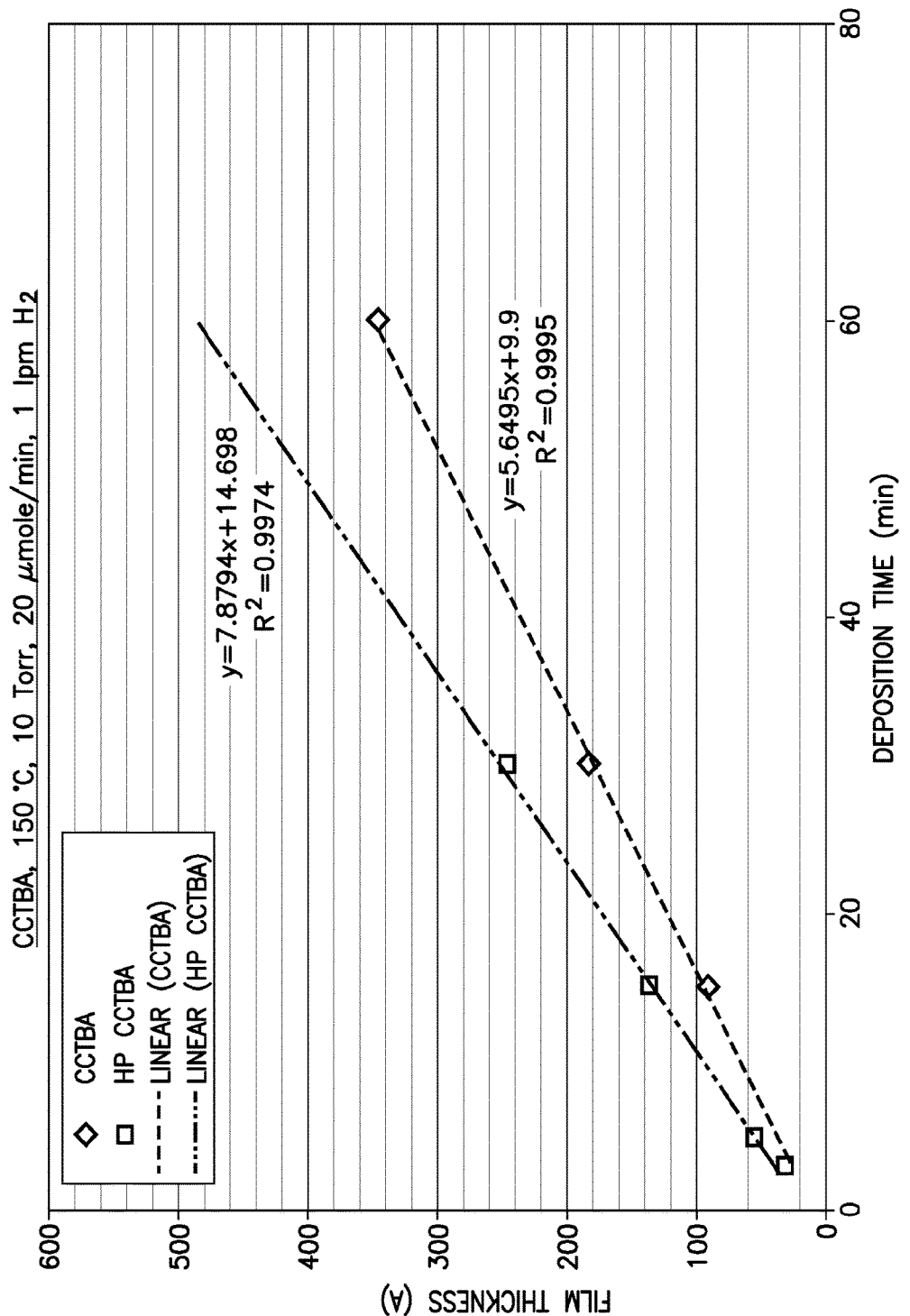

FIG. 30 is a graph of film thickness, in Angstroms, as a function of deposition time, in minutes, for cobalt films deposited using non-purified CCTBA precursor and high purity (HP) CCTBA precursor, at a deposition temperature of 150° C., a deposition pressure of 10 torr, a precursor flow rate of 20 μmoles/minute, and a flow rate of 1 liter per minute of co-reactant hydrogen.

DETAILED DESCRIPTION

The present disclosure relates to high purity, low resistivity cobalt and articles comprising same, and precursors and processes for forming such high purity, low resistivity cobalt on substrates.

As used herein and in the appended claims, the singular forms "a", "and", and "the" include plural referents unless the context clearly dictates otherwise.

As used herein, the term "film" refers to a layer of deposited material having a thickness below 1000 micrometers, e.g., from such value down to atomic monolayer thickness values. In various embodiments, film thicknesses of deposited material layers in the practice of the disclosure may for example be below 100, 10, or 1 micrometer(s), or in various thin film regimes below 200, 10 or 1 nanometer(s), depending on the specific application involved. As used herein, the term "thin film" means a layer of a material having a thickness below 1 micrometer, however it will be recognized that cobalt-containing material in the broad practice of the present disclosure may have any suitable thickness for the application that is involved.

"CCTBA" as used herein refers to dicobalt hexacarbonyl tert-butylacetylene, or to a derivative of dicobalt hexacarbonyl tert-butylacetylene as hereinafter described. Dicobalt hexacarbonyl tert-butylacetylene has the formula $Co_2(CO)_6(HCC(CH_3)_3)$,

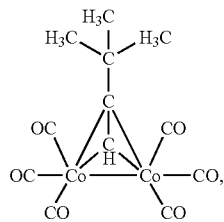

with a boiling point of 52° C. at 0.8 torr (106.7 Pa), and exists as a red liquid at 25° C.

"CCTMSA" as used herein refers to dicobalt hexacarbonyl trimethylsilyl acetylene (CCTMSA), having the formula

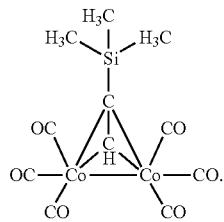

"CCBTMSA" as used herein refers to cobalt carbonyl bis(trimethylsilyl acetylene), having the formula $[((H_3C)Si)C\equiv C]_2Co(CO)$.

The disclosure, as variously set out herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the disclosure. The disclosure correspondingly contemplates such features, aspects and embodiments, or a selected one or ones thereof, in various permutations and combinations, as being within the scope of the present disclosure.

As used herein, the term "high purity" refers to cobalt films containing less than 5 at % carbon and less than 3 at % oxygen in the cobalt film.

The term "low resistivity" as used herein refers to cobalt films having a resistivity that is less than 50 $\mu\Omega$-cm.

In one aspect, the present disclosure relates to a cobalt deposition process, comprising:
volatilizing a cobalt precursor selected from among CCTBA, CCTMSA, and CCBTMSA, to form a precursor vapor; and
contacting the precursor vapor with a substrate under vapor deposition conditions effective for depositing on the substrate (i) high purity, low resistivity cobalt or (ii) cobalt that is annealable by thermal annealing to form high purity, low resistivity cobalt.

Thus, in various embodiments, the vapor deposition conditions may be effective for depositing the high purity, low resistivity cobalt on the substrate, without necessity of subsequent annealing or other post-deposition processing. In other embodiments, the vapor deposition conditions are effective for depositing on the substrate cobalt that is annealable by thermal annealing to form the high purity, low resistivity cobalt, and the deposited cobalt is annealed by thermal annealing to form high purity, low resistivity cobalt.

In various embodiments of such process, the CCTBA, CCTMSA, or CCBTMSA cobalt precursor is volatilized by vaporization of a solvent solution thereof. The solvent solution may for example comprise an organic solvent, such as a hydrocarbon solvent, e.g., a solvent selected from the group consisting of alkane solvents, aromatic solvents, ketone solvents, ether solvents, etc. In various embodiments, the solvent may comprise an alkane solvent, e.g., a $C_4$-$C_{10}$ alkane solvent, such as butane, pentane, hexane, heptane, octane, nonane, or decane, or, more generally, any other solvent species, solvent mixture, etc. that is compatible with the cobalt precursor.

The process of the present disclosure may be conducted, in various embodiments, with the precursor vapor being transported in a carrier gas to the contacting step in which the precursor vapor/carrier gas mixture is contacted with the substrate to effect deposition of cobalt on the substrate. The carrier gas may be of any suitable type, and may include any suitable carrier gas or gases that are compatible with the precursor vapor. The carrier gas may for example comprise an inert or other suitable gas, such as argon, neon, xenon, krypton, helium, hydrogen, etc.

The vapor deposition conditions in the above-described process may in various embodiments comprise pressure in a suitable range, e.g., a range of from 2 to 1200 torr, a range of from 2 to 100 torr, a range of from 5 to 100 torr, a range of from 5 to 70 torr, a range of from 10 to 50 Torr, or pressure in other suitable pressure range. The vapor deposition conditions in various embodiments may comprise temperature in a range of from 25° C. to 400° C., a range of from 60° C. to 200° C., a range of from 100° C. to 200° C., a range of from 120° C. to 175° C., a range of from 125° C. to 165° C., or temperature in other suitable temperature range.

CCTBA may be volatilized in the process to form the precursor vapor, in various embodiments. In other embodiments, CCTMSA may be volatilized in the process to form the precursor vapor. The precursor vapor may be mixed with co-reactants and/or carrier gases, for delivery to the contacting of the precursor vapor with the substrate. The substrate may be of any suitable type, and may for example comprise a semiconductor substrate, such as a silicon oxide substrate, a metal substrate, e.g., copper or tungsten substrate, glass, ceramic, or other appropriate substrate for the specific product to be formed comprising the cobalt film.

The contacting of the precursor vapor with the substrate in processes of the disclosure may be carried out for any suitable period of time, e.g., a period of from 2 to 60 minutes, a period of from 3 to 15 minutes, a period of from 5 to 12 minutes, or other suitable period of time. In various embodiments, the contacting is conducted for a period of time sufficient to deposit a predetermined thickness of the deposited cobalt. Such thickness may be of any suitable magnitude, e.g., a thickness in a range of from 2 nm to 1000 nm, a thickness in a range of from 2 nm to 500 nm, a thickness in a range of from 4 nm to 400 nm, a thickness in a range of from 5 nm to 300 nm, or thickness in other thickness range.

In various embodiments, the cobalt film after the contacting is annealed by a thermal annealing process. The thermal annealing can be carried out at any suitable annealing conditions, e.g., temperature in a range of from 200° C. to 600° C., a range of from 200° C. to 550° C., a range of from 350° C. to 550° C., a range of from 375° C. to 450° C., or temperature in other suitable temperature range.

In various embodiments of the process of the present disclosure, the thermal annealing can be conducted for a suitable period of time to achieve a desired resistivity and other desired characteristics of the film. For example, the annealing can be carried out for a period in a range of from 1 minute to 20 minutes, in a range of from 2 minutes to 15 minutes, in a range of from 10 to 12 minutes, or other period of time. The thermal annealing may be conducted for a period that is effective to reduce resistivity of the cobalt film as deposited on the substrate, e.g., by an amount in a range of from 25% to 90% of the as-deposited resistivity of the cobalt film, in a range of from 30% to 80% reduction, in a range of from 40% to 75% reduction, or in other range of reduction of resistivity, to yield a desired resistivity value, e.g., a resistivity in a range of from 10 to 40 $\mu\Omega$-cm.

The cobalt film formed by processes of the present disclosure has high purity and low resistivity, e.g., a resistivity in a range of from 2 to 48 $\mu\Omega$-cm, a range of from 10 to 45 $\mu\Omega$-cm, a range of from 15 to 40 $\mu\Omega$-cm, a range of from 18 to 38 $\mu\Omega$-cm, or resistivity in other suitable range.

In specific embodiments of the process of the present disclosure, the contacting of the precursor vapor with the substrate may be carried out with delivery of the precursor vapor to the substrate at a suitable rate to achieve the desired deposited cobalt thickness and other properties. In specific embodiments, the precursor vapor maybe flowed to the substrate for contacting thereof, at a flow rate that is in a range of from 20 to 100 $\mu$moles/minute. The cobalt precursor may be flowed to the contacting step in the mixture with hydrogen or other co-flow gas or gases. Such a co-flow gases may be delivered at any suitable rate, e.g., a rate in a range of from 1 to 5 L per minute, or other suitable flow rate. The contacting may be carried out at pressure in a range of from 10 to 50 torr in various specific embodiments. Cobalt may be deposited on the substrate from the precursor vapor at any suitable deposition rate, such as a deposition rate in a range of from 2 to 20 Å/minute, a deposition rate in a range of from 1 to 10 Å/minute, or other deposition rate.

The cobalt film in various embodiments of the present invention can be formed at any suitable thickness, e.g., a thickness in a range of from 75 Å to 500 Å, a thickness in a range of from 10 Å to 400 Å, a thickness in a range of from 20 Å to 300 Å, or thickness in another range.

The processes of the present disclosure may be carried out to produce cobalt films of superior electrical character, e.g., cobalt films having a current density in a range of from $10^{-1}$ to $10^{-6}$ amperes/cm$^2$ at a voltage of 0.5V.

In specific embodiments of the process of the present disclosure, the cobalt precursor is volatilized to form the precursor vapor, and the cobalt film deposited on the substrate is annealed by a thermal annealing process. The thermal annealing process in such application may be conducted for any suitable period of time and at any suitable temperature. In illustrative embodiments, the annealing may be conducted for a period of from 1 minute to two hours at temperature in a range of from 150° C. to 500° C., e.g., or for a period of from 1 to 15 minutes at temperature in a range of from 375° C. to 450° C., or under other suitable time and temperature conditions.

The cobalt films of the present disclosure as formed by method comprising the process according to any of the previously described embodiments can be utilized to form devices comprising the high purity, low resistivity cobalt films. Such devices may be of any suitable type, and in various embodiments may comprise a semiconductor device, flat-panel display, or solar panel. The present disclosure therefore contemplates a thin-film structure comprising a vapor-deposited high purity, low resistivity cobalt film, such as a high purity, low resistivity cobalt film formed by a method comprising a process according to any of the embodiments and aspects described hereinabove.

Concerning the cobalt precursors of the present disclosure, CCTBA, CCTMSA, and CCBTMSA have similar volatilization and transport properties. For example, CCTBA has a T50 of 146.8° C. with a residue of 10.5% (6.8% after purification) and 0.1 torr vapor pressure at 40° C., and CCTMSA has a T50 of 143° C. and a residue of 8%.

Set out below is a description of various specific embodiments, aspects, and features of the present disclosure, which illustrate particular implementations of the processes and methods, and cobalt precursors, of the present disclosure.

In one such implementation, cobalt films were deposited using CCTMSA as the precursor for chemical vapor deposition of the cobalt films. A starting precursor solution of 0.02 M concentration of the precursor in octane was used. The precursor solution was delivered at a flow rate of 0.1 cc/minute to a vaporizer maintained at temperature of 50° C. for volatilization of the precursor. The resulting precursor vapor was delivered to the deposition chamber by helium carrier gas at a flow rate of 100 sccm, and co-reactant flow of hydrogen ($H_2$) at flow rate of 1 liter per minute (lpm). The deposition chamber pressure was 10 torr, with a deposition temperature of 150° C. and a chamber body temperature of 50° C. Deposition was carried out for 15 minutes. Thin conductive cobalt films were formed, having silicon content of approximately 0.27 atomic %, as determined from x-ray fluorescence (XRF) determination.

Figure 1:
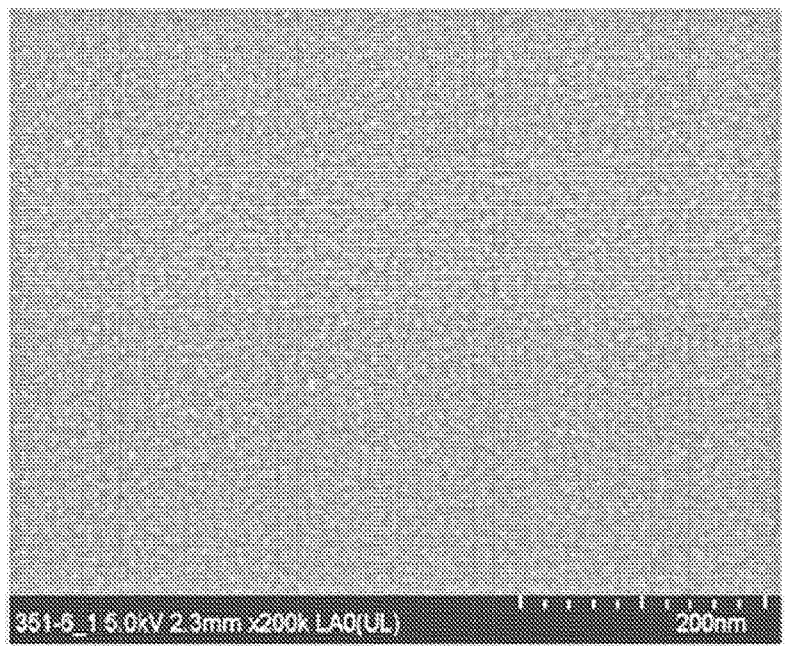
FIG. 1 is a scanning electron microscope (SEM) micrograph at magnification of 200,000 times, showing a smooth conformal 13 Angstrom thick film of cobalt as having been formed by CVD of cobalt using a CCTMSA precursor.

FIG. 1 is a scanning electron microscope (SEM) micrograph at magnification of 200,000 times, showing a smooth conformal 13 Angstrom thick film of cobalt as having been formed by CVD of cobalt using the CCTMSA precursor under the foregoing conditions.

Figure 2:
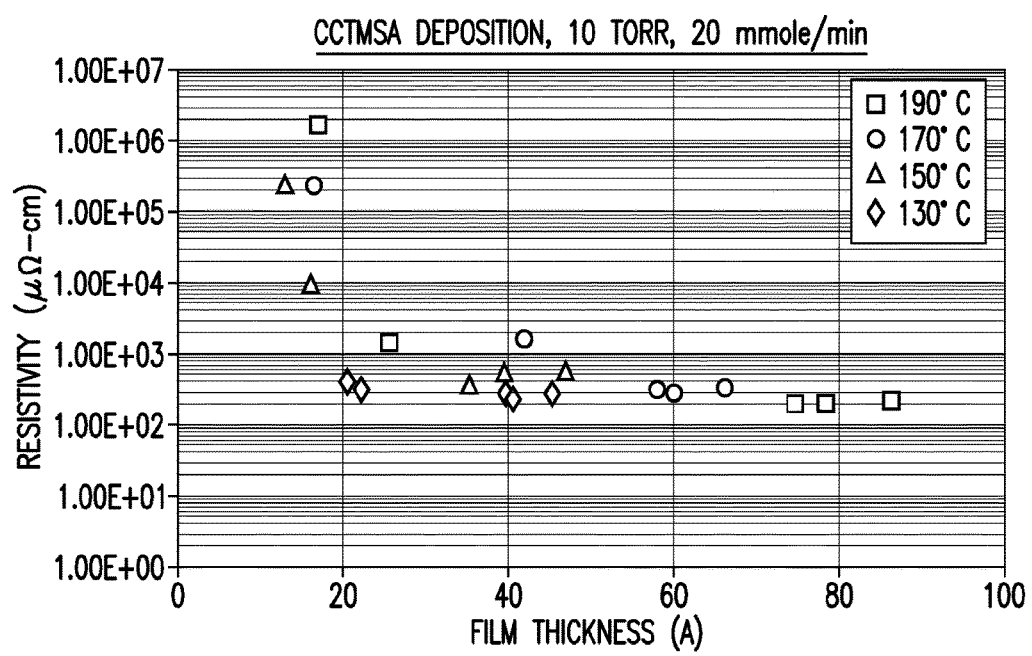
FIG. 2 is a graph of resistivity, in µΩ-cm, as a function of cobalt film thickness, in Angstroms, for cobalt films deposited at varying temperature, of 130° C., 150° C., 170° C., and 190° C., using CCTMSA as a precursor, at a precursor feed rate of 20 µmoles/minute, and pressure of 10 torr.

FIG. 2 is a graph of resistivity, in $\mu\Omega$-cm, as a function of cobalt film thickness, in Angstroms, for films deposited at varying temperature, of 130° C., 150° C., 170° C., and 190° C., using CCTMSA as a precursor, at a precursor feed rate of 20 $\mu$moles/minute, and pressure of 10 torr. The data show that higher temperature and film thickness produced lower film resistivity values. For comparison, a 9 nm thick cobalt film formed using CCTBA as the precursor exhibited a film resistivity on the order of about 24 $\mu\Omega$-cm.

Figure 3:
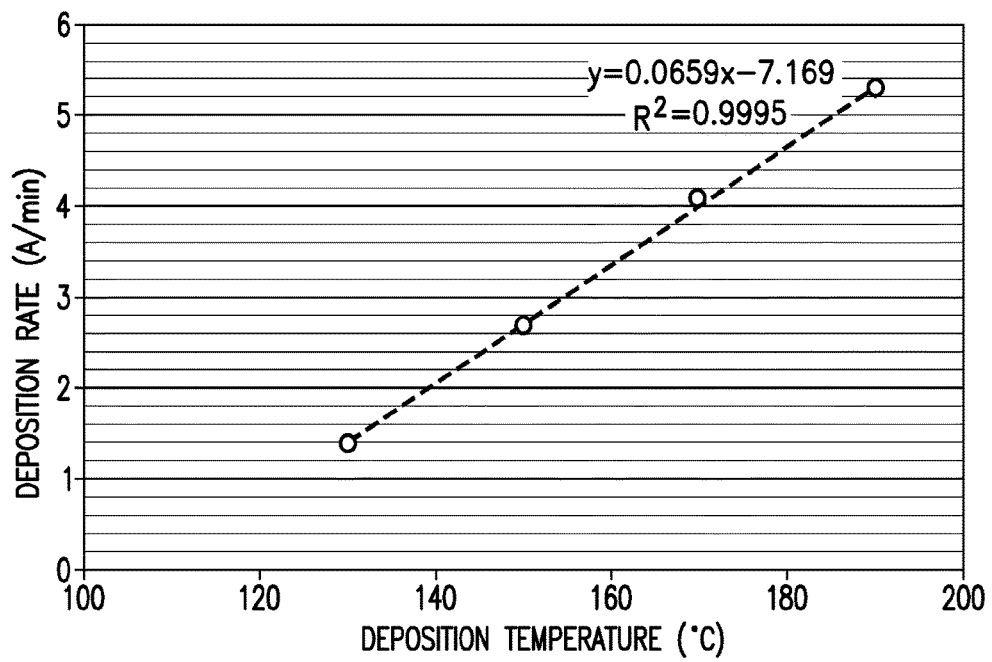
FIG. 3 is a graph of deposition rate, in Angstroms per minute, as a function of deposition temperature, in ° C., for cobalt films formed using CCTMSA as a precursor, at a pressure of 10 torr, and a precursor feed rate of 20 µmole/minute.

The effect of temperature on deposition rate is shown in FIG. 3, which is a graph of deposition rate, in Angstroms per minute, as a function of deposition temperature, in ° C. for cobalt films formed using CCTMSA as a precursor, at a pressure of 10 torr, and a precursor feed rate of 20 $\mu$mole/minute. The data show that the deposition rate increases with increasing temperature.

Figure 4:
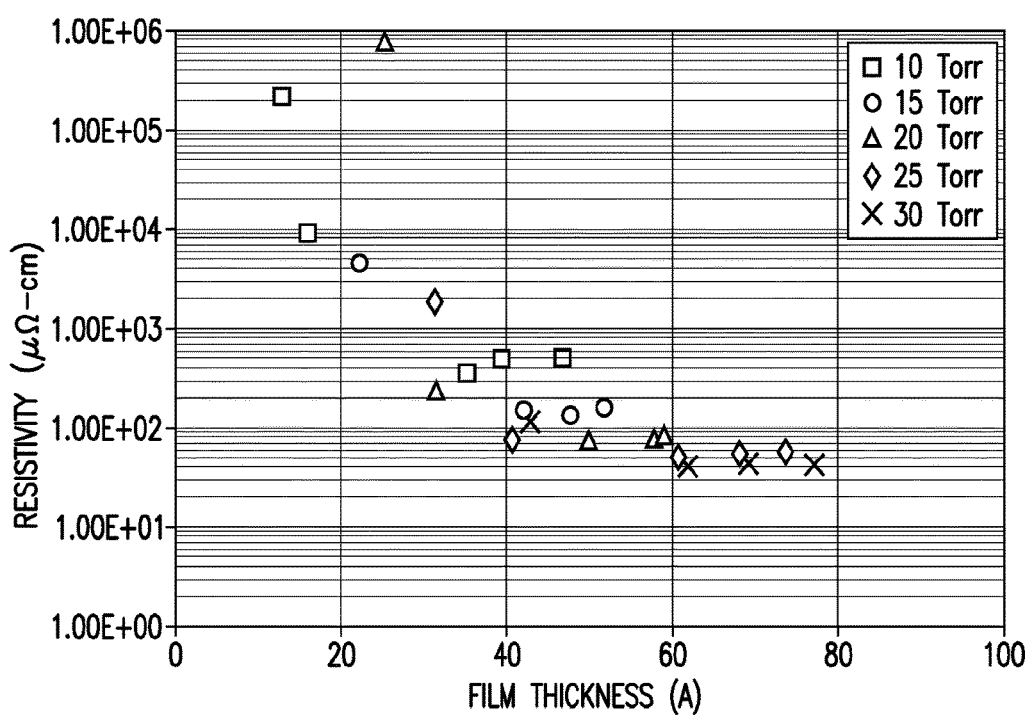
FIG. 4 is a graph of resistivity, in µΩ-cm, as a function of film thickness, in Angstroms, for cobalt films formed at varying pressures, of 10 torr, 15 torr, 20 torr, and 30 torr, using CCTMSA as a cobalt precursor at a deposition temperature of 150° C., and a precursor feed rate of 20 µmoles/minute.

FIG. 4 is a graph of resistivity, in $\mu\Omega$-cm, as a function of film thickness, in Angstroms, for cobalt films formed at varying pressures, of 10 torr, 15 torr, 20 torr, and 30 torr, using CCTMSA as a cobalt precursor at a deposition temperature of 150° C., and a precursor feed rate of 20 µmoles/minute.

Figure 5:
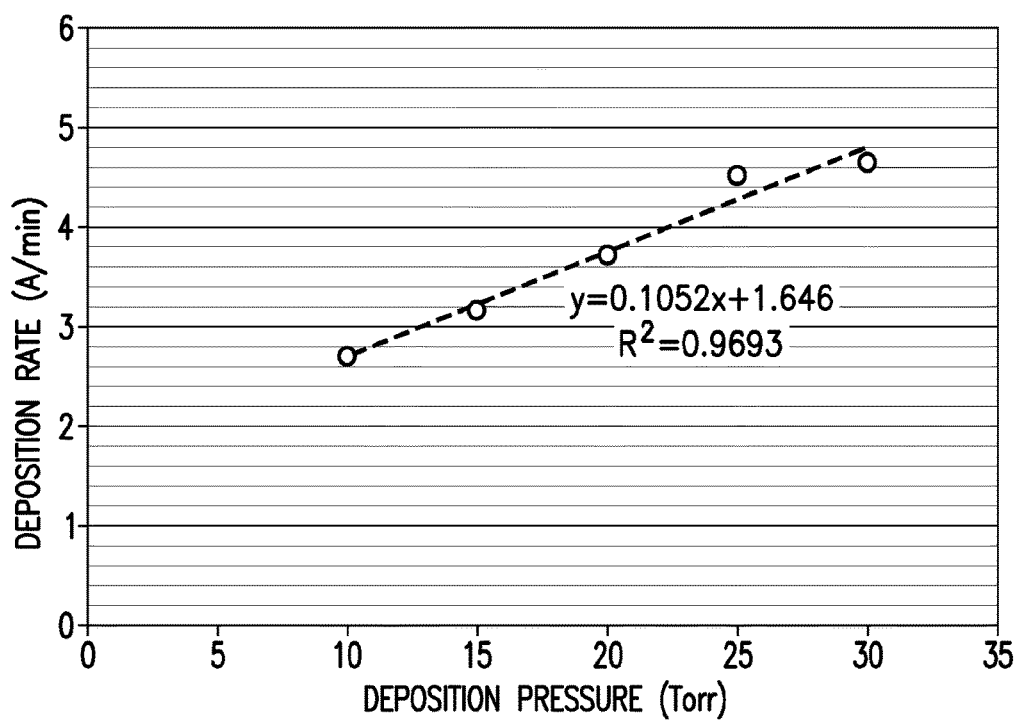
FIG. 5 is a graph of deposition rate, in Angstroms per minute, as a function of deposition pressure, in torr, for cobalt films formed using CCTMSA as a precursor, at temperature of 150° C., and precursor feed rate of 20 µmoles/minute.

FIG. 5 is a graph of deposition rate, in Angstroms per minute, as a function of deposition pressure, in torr, for cobalt films formed using CCTMSA as a precursor, at temperature of 150° C., and precursor feed rate of 20 µmoles/minute.

The data in FIGS. 4 and 5 show that deposition rate increases and resistivity decreases with increasing film thickness. A resistivity of approximately 40 µΩ-cm at 150° C. and 30 torr pressure was achieved for a 6.2 nm thick cobalt film.

At temperature of 190° C. and pressure of 30 torr, the deposition rate dropped to 3.54 Angstroms/minute, and the films became non-conductive.

Figure 6:
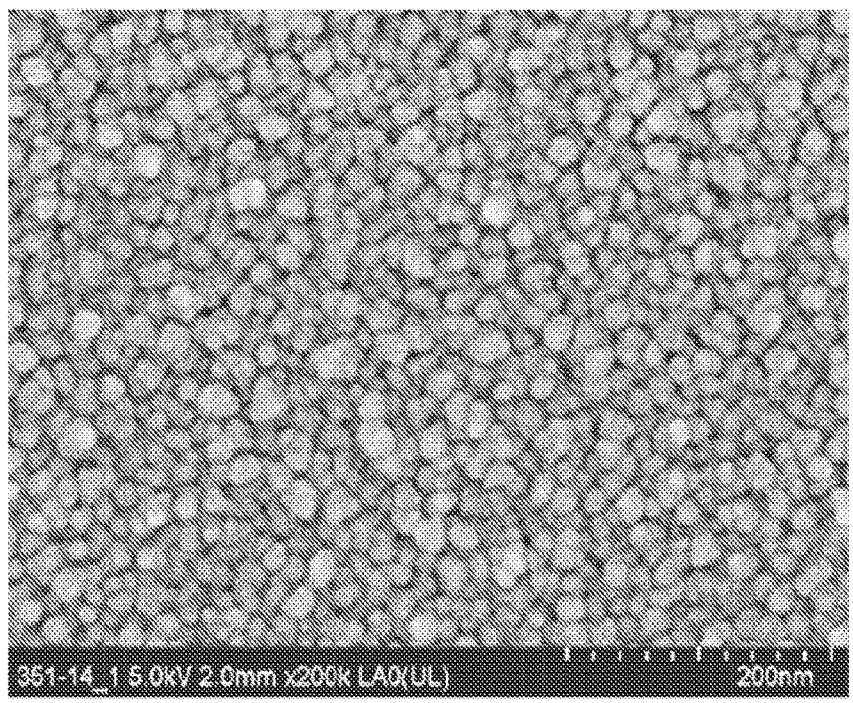
FIG. 6 is a micrograph of a visually rough cobalt film at a thickness of 28 nm, as formed by deposition of cobalt at temperature of 150° C. and pressure of 30 torr, for a period of 30 minutes.
Figure 7:
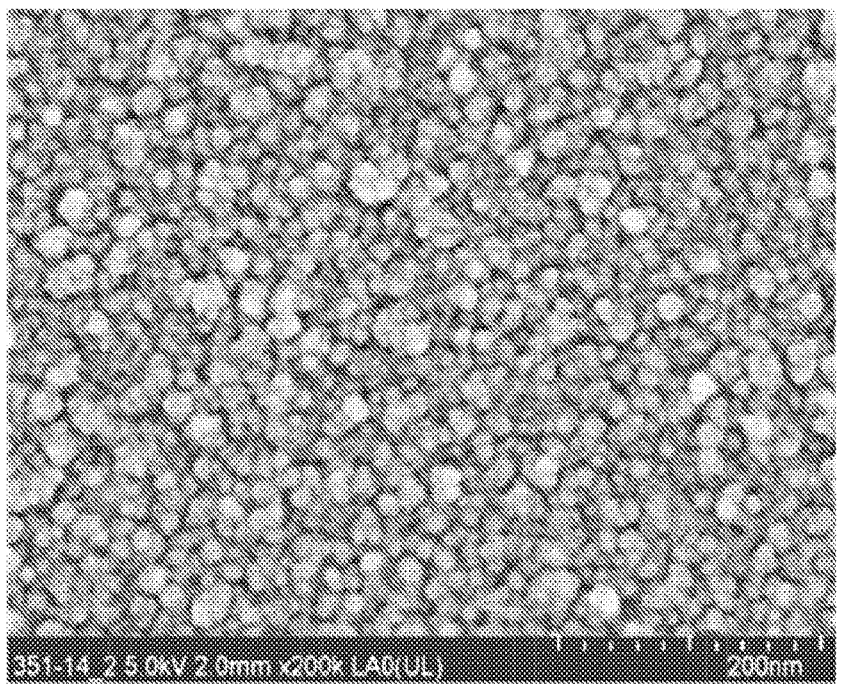
FIG. 7 shows a micrograph of a visually rough cobalt film at a thickness of 27 nm, as formed by cobalt deposition at temperature of 150° C. and pressure of 25 torr, for a period of 60 minutes.

Thicker film samples were then prepared for SIMS (secondary ion mass spectrometry) analysis, using CCTMSA as the precursor. FIG. 6 shows a micrograph of a visually rough cobalt film at a thickness of ~28 nm, as formed by deposition of cobalt at temperature of 150° C. and pressure of 30 torr, for a period of 30 minutes. After deposition, the film was subjected to rapid thermal annealing (RTN) in nitrogen for one minute at 400° C. The resistivity of the film as deposited was 34 µΩ-cm, and this resistivity was reduced to 16.7 µΩ-cm by the RTN treatment. FIG. 7 shows a micrograph of a visually rough cobalt film at a thickness of 27 nm, as formed by cobalt deposition at temperature of 150° C. and pressure of 25 torr, for a period of 60 minutes. The resistivity of the film as deposited was 47 µΩ-cm.

In general, RTN treatment at 400° C. is able to achieve a substantial reduction in resistivity of the vapor-deposited cobalt films, using CCTMSA as the precursor, as shown for the samples tested in Table 1 below.

TABLE 1

| Sample ID | XRF Thickness (A) | As-dep Sheet Resistance (ohm/Sq) | As-dep Resistivity (µohm-cm) | 400 C. RTN Sheet R (ohm/Sq) | Calculated RTN Resistivity (µohm-cm) | % Reduction in Resistivity |
|---|---|---|---|---|---|---|
| 101513B-C | 35.2 | 1009 | 355.2 | 119.10 | 41.9 | 88.2 |
| 101713B-C | 58.1 | 131.7 | 76.5 | 38.79 | 22.5 | 70.5 |
| 101813A-C | 77.5 | 54.7 | 42.4 | 25.4 | 19.7 | 53.6 |
| 102113A-BL | 281.1 | 12.03 | 33.8 | 5.956 | 16.7 | 50.5 |

As shown, the resistivity of the films was reduced by approximately 50-90% by the RTN treatment at 400° C. For purposes of comparison, the resistivity of a corresponding cobalt film deposited at thickness of 3.5 nm was determined to be <50 µΩ-cm.

The deposition of cobalt via vapor deposition using CCTMSA as a cobalt precursor can be carried out in various embodiments at process conditions including co-flow of hydrogen as a co-reactant with the precursor, at pressures that may for example be on the order of 10-50 torr, with precursor delivery rate in a range of from 20 to 100 µmole/minute, and hydrogen flow rate of from 1000 to 5000 sccm, to achieve deposition rates of cobalt that may be in a range of from 2 to 20 or more Angstroms/minute. Table 2 below shows the resistivity in µΩ-cm of 10 nm thick cobalt films formed using CCTMSA as the precursor under such conditions.

TABLE 2

| Pressure, torr | Delivery, µmole/min. | H₂ Flow, sccm | Resistivity, µΩ-cm |
|---|---|---|---|
| 10 | 20 | 1000 | 219.6 |
| 10 | 20 | 5000 | 93 |
| 10 | 100 | 1000 | 5332 |
| 10 | 100 | 5000 | 396 |
| 50 | 20 | 1000 | 34.6 |
| 50 | 20 | 5000 | 71.1 |
| 50 | 100 | 1000 | 57.4 |
| 50 | 100 | 5000 | 51.3 |

The data in Table 2 show that higher pressure of 50 torr and higher CCTMSA precursor delivery rate of 100 µmole/minute were most beneficial in achieving the lowest resistivity values in the as-deposited films, and that the variation in flow rate of the hydrogen co-reactant gas had little effect on the resistivity value that was obtained for the deposited film.

Figure 8:
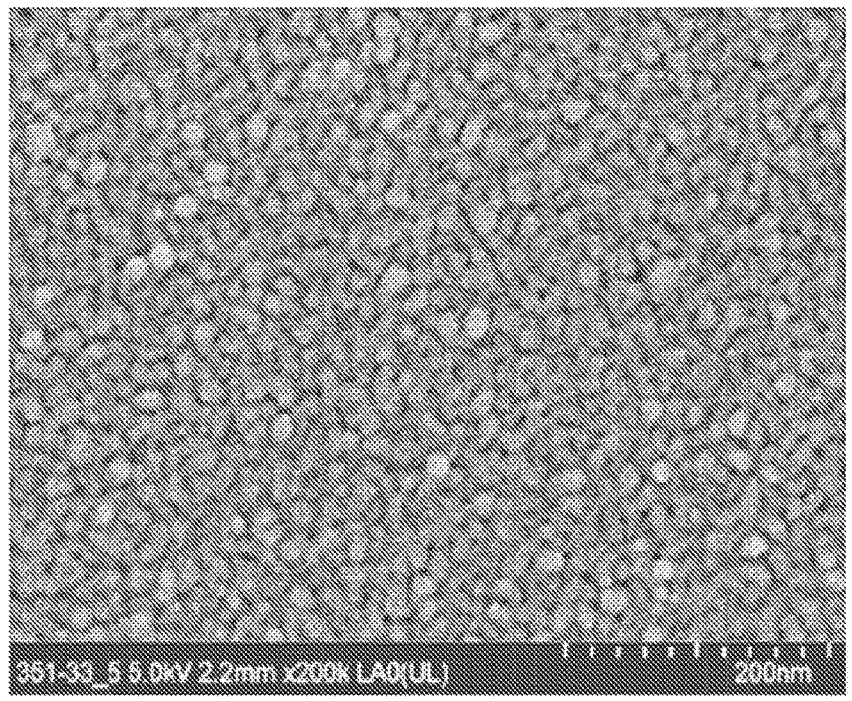
FIG. 8 is a SEM micrograph of a cobalt film deposited at 50 torr pressure, at a precursor flow rate of 20 μmoles/minute, and 1 liter per minute flow of H$_2$, in which the film had a thickness of 95.2 Angstroms, and a resistivity of 34.5 μΩ-cm.
Figure 9:
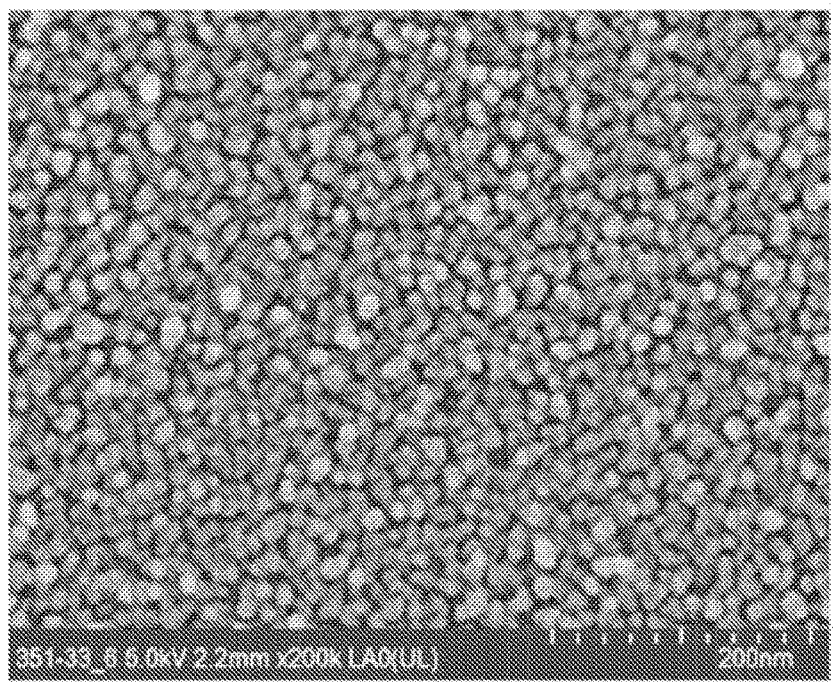
FIG. 9 is a SEM micrograph of a cobalt film deposited at 50 torr pressure, at a precursor flow rate of 20 μmoles/minute, and 5 liters per minute flow of H$_2$, in which the film had a thickness of 99.8 Angstroms, and a resistivity of 79.7 μΩ-cm.
Figure 10:
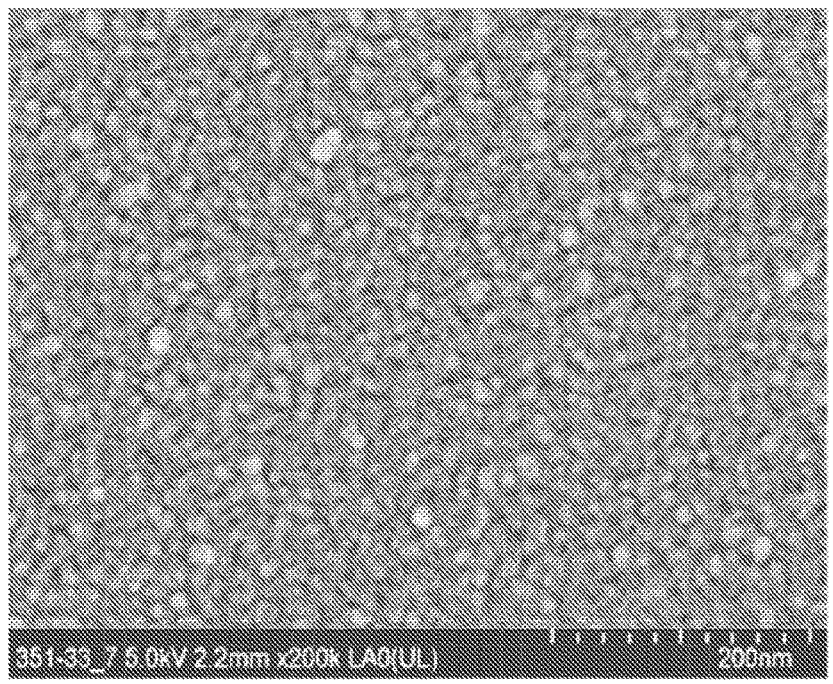
FIG. 10 is a SEM micrograph of a cobalt film deposited at 50 torr pressure, at a precursor flow rate of 100 μmoles/minute, and 1 liter per minute flow of H$_2$, in which the film had a thickness of 97.7 Angstroms, and a resistivity of 57.5 μΩ-cm.
Figure 11:
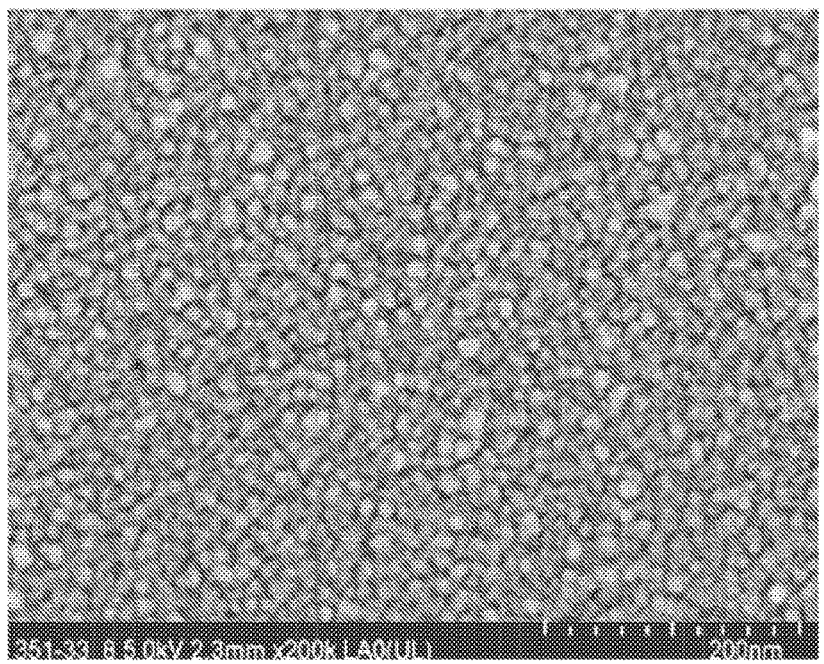
FIG. 11 is a SEM micrograph of a cobalt film deposited at 50 torr pressure, at a precursor flow rate of 100 μmoles/minute, and 5 liters per minute flow of H$_2$, in which the film had a thickness of 111.2 Angstroms, and a resistivity of 52.4 μΩ-cm.

SEM micrographs of cobalt films formed at 50 torr pressure are shown in FIGS. 8-11. FIG. 8 is a SEM micrograph of a cobalt film deposited at 50 torr pressure, at a precursor flow rate of 20 µmoles/minute, and 1 liter per minute flow of H₂, in which the film had a thickness of 95.2 Angstroms, and a resistivity of 34.6 µΩ-cm. FIG. 9 is a SEM micrograph of a cobalt film deposited at 50 torr pressure, at a precursor flow rate of 20 µmoles/minute, and 5 liters per minute flow of H₂, in which the film had a thickness of 99.8 Angstroms, and a resistivity of 71.1 µΩ-cm. FIG. 10 is a SEM micrograph of a cobalt film deposited at 50 torr pressure, at a precursor flow rate of 100 µmoles/minute, and 1 liter per minute flow of H₂, in which the film had a thickness of 97.7 Angstroms, and a resistivity of 57.4 µΩ-cm. FIG. 11 is a SEM micrograph of a cobalt film deposited at 50 torr pressure, at a precursor flow rate of 100 µmoles/minute, and 5 liters per minute flow of H₂, in which the film had a thickness of 111.2 Angstroms, and a resistivity of 51.3 µΩ-cm.

Table 3 below shows data for a series of cobalt film samples that were deposited at 50 torr pressure, including XRF thickness of the film, as-deposited sheet resistance, in ohm/Sq, the as-deposited resistivity, in µΩ-cm, the sheet resistance, in ohm/Sq, after rapid thermal anneal (RTN) at 400° C., corresponding resistivity after RTN, and % resistivity reduction.

TABLE 3

| XRF Thickness (A) | As-dep Sheet Resistance (ohm/Sq) | As-dep Resistivity (μohm-cm) | 400 C. RTN Sheet R (ohm/Sq) | Calculated RTN Resistivity (μohm-cm) | % Reduction in Resistivity | Pressure (Torr) |
|---|---|---|---|---|---|---|
| 72.8 | 53.91 | 39.2 | 29.61 | 21.6 | 45.1 | 50 |
| 82.8 | 50.96 | 42.2 | 25.62 | 21.2 | 49.7 | 50 |
| 61 | 79.23 | 48.3 | 64.59 | 39.4 | 18.5 | 50 |
| 102.1 | 27.46 | 28.0 | 21.09 | 21.5 | 23.2 | 50 |
| 236 | 11.56 | 27.3 | 6.674 | 15.8 | 42.3 | 50 |
| 150.6 | 18.78 | 28.3 | 12.42 | 18.7 | 33.9 | 50 |
| 147.2 | 18.88 | 27.8 | 11.63 | 17.1 | 38.4 | 50 |
| 166.5 | 13.76 | 22.9 | 8.067 | 13.4 | 41.4 | 50 |
| 180.4 | 12.4 | 22.4 | 9.41 | 17.0 | 24.1 | 50 |
| 137.9 | 18.55 | 25.6 | 13.08 | 18.0 | 29.5 | 50 |

The data in Table 3 were generated for films formed by vapor deposition of cobalt using CCTMSA as a precursor, at a precursor flow rate of 20 μmoles/minute, a deposition temperature of 150° C., 50 torr pressure, and 1 liter per minute flow of co-reactant hydrogen, and deposition rate that was on the order of 6.5 Angstroms per minute.

The data in Table 3 show that 400° C. RTN treatment of the films having low as-deposited resistivity resulted in further resistivity reductions of approximately 20 to 50%, with absolute values of resistivity after 400° C. RTN treatment that ranged from 13.4 to 39.4 μΩ-cm.

Table 4 below shows corresponding data for cobalt films that were deposited at high rates of up to 27 Angstroms per minute, by vapor deposition of cobalt using CCTMSA as a precursor, at a precursor flow rate of 100 μmoles/minute, a deposition temperature of 150° C., 50 torr pressure, and 5 liters per minute flow of co-reactant hydrogen.

TABLE 4

| XRF Thickness (A) | As-dep Sheet Resistance (ohm/Sq) | As-dep Resistivity (μohm-cm) | 400 C. RTN Sheet R (ohm/Sq) | Calculated RTN Resistivity (μohm-cm) | % Reduction in Resistivity | Pressure (Torr) |
|---|---|---|---|---|---|---|
| 329.9 | 12.82 | 42.3 | 6.484 | 21.4 | 49.4 | 50 |
| 406.6 | 10.68 | 43.4 | 4.914 | 20.0 | 54.0 | 50 |
| 156.7 | 36.64 | 57.4 | 18.91 | 29.6 | 48.4 | 50 |
| 343.1 | 12.81 | 44.0 | 7.151 | 24.5 | 44.2 | 50 |
| 120.8 | 37.14 | 44.9 | 14.42 | 17.4 | 61.2 | 50 |
| 78.1 | 86.5 | 67.6 | 36.57 | 28.6 | 57.7 | 50 |
| 286.9 | 16.02 | 46.0 | 7.191 | 20.6 | 55.1 | 50 |
| 54.8 | 133.3 | 73.0 | 66.84 | 36.6 | 49.9 | 50 |

The Table 4 data show that 400° C. RTN treatment of the films having low as-deposited resistivity resulted in further resistivity reductions of approximately 45 to 61%, with absolute values of resistivity after 400° C. RTN treatment that ranged from 17.4 to 36.6 μΩ-cm.

Figure 12:
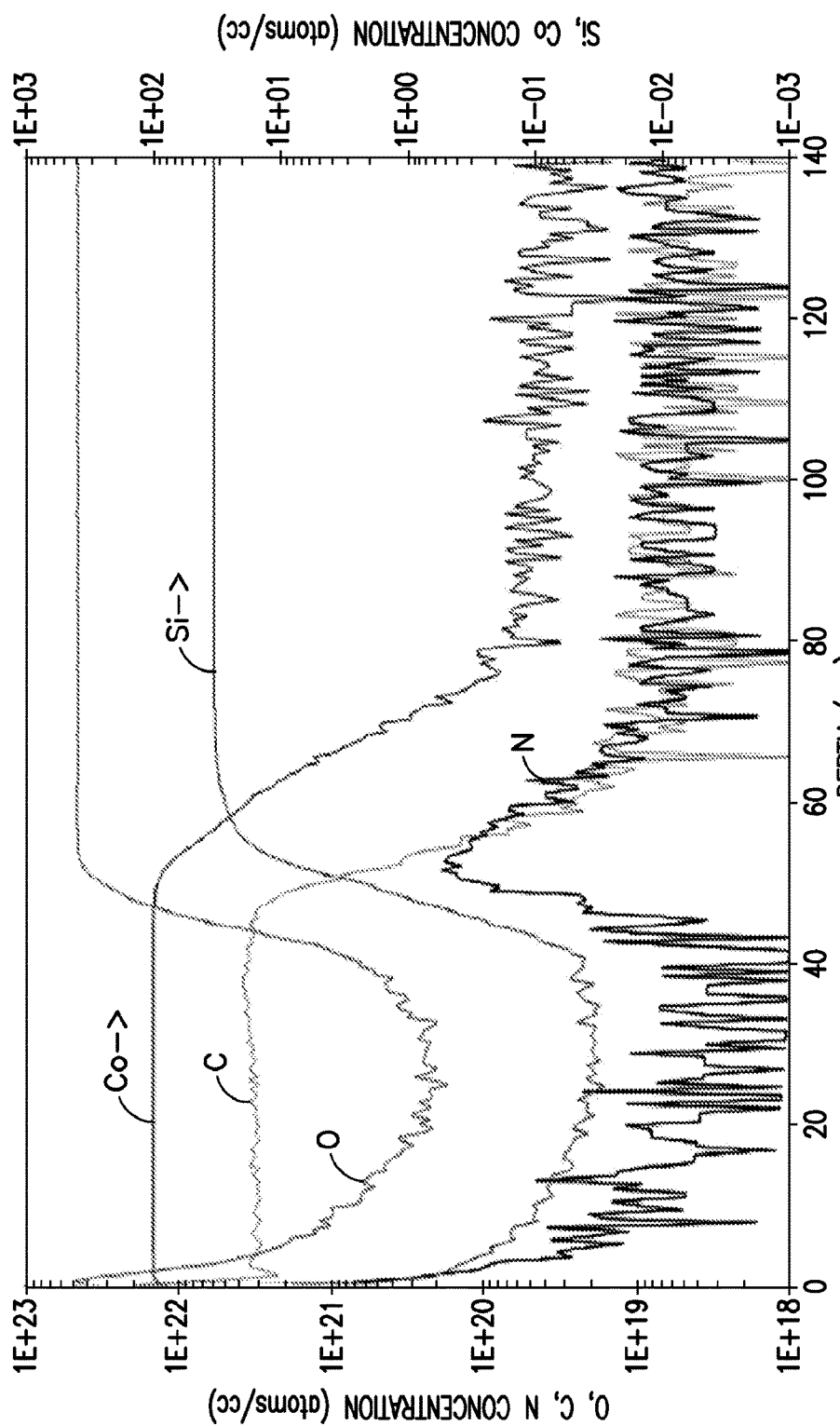
FIG. 12 is a SIMS plot for a cobalt film formed by vapor deposition of cobalt using CCTMSA as a precursor, at a precursor flow rate of 20 μmoles/minute, a deposition temperature of 150° C., 30 torr pressure, and 1 liter per minute flow of co-reactant hydrogen, in which the SIMS plot shows the concentrations of Si, Co, O, C, and N, in atoms/cc, as a function of depth, in nanometers.

SIMS analysis was conducted on a cobalt film formed by vapor deposition of cobalt using CCTMSA as a precursor, at a precursor flow rate of 20 μmoles/minute, a deposition temperature of 150° C., 30 torr pressure, and 1 liter per minute flow of co-reactant hydrogen. The film exhibited some pinhole and particles, had a resistivity of 30.3 μΩ-cm, and contained 3.33 at % carbon. The SIMS plot is shown in FIG. 12, with concentrations of Si, Co, O, C, and N being shown, in atoms/cc, as a function of depth, in nanometers.

Cobalt MOCVD was carried out using CCTBA as a precursor. The CCTBA precursor had a T50 temperature of 146.8° C., a residue of 10.5% (6.8% after purification) and a 0.1 torr vapor pressure at 40° C. The deposition conditions included a concentration of 0.1 M of the CCTBA precursor in octane, delivery of the precursor at 0.2 μmoles/minute, a deposition temperature of 150° C., a chamber body temperature of 70° C., a chamber pressure of 10 torr, a vaporizer temperature of 70° C., a helium carrier gas flow rate of 100 sccm, a hydrogen co-reactant flow rate of 1 liter per minute (lpm), and a deposition period of 6 minutes. The results are shown in Table 5 below.

TABLE 5

| XRF Thickness (A) | Sheet R (Ω/Sq) | Resistivity (μΩ-cm) |
|---|---|---|
| 177.4 | 22.93 | 40.67 |
| 89.8 | 40.31 | 36.19 |

TABLE 5-continued

| XRF Thickness (A) | Sheet R (Ω/Sq) | Resistivity (μΩ-cm) |
|---|---|---|
| 156.9 | 25.27 | 39.65 |
| 174.8 | 23.69 | 41.41 |
| 83.6 | 47.96 | 40.09 |

The data in Table 5 show good resistivity character of the cobalt films deposited from CCTBA.

Cobalt films at higher thickness were then deposited at precursor flow rate of 200 μmoles/minute, with the results shown in Table 6.

TABLE 6

| XRF Thickness (Å) | Sheet R (Ω/Sq) | Resistivity (μΩ-cm) |
|---|---|---|
| 487.4 | 8.5 | 41.4 |
| 289.5 | 13.41 | 38.8 |
| 421.7 | 9.45 | 39.9 |
| 464.4 | 9.07 | 42.1 |
| 219.7 | 15.81 | 34.7 |

These results showed that at higher thicknesses, the sheet resistance (Ω/Sq) was significantly reduced (compare Table 5) than the sheet resistance at low thicknesses, and resistivity in all cases was less than 45 μΩ-cm.

Cobalt films were then deposited using CCTBA as the cobalt precursor, at a flow rate of 100 μmoles/minute, with the results set out in Table 7.

TABLE 7

| XRF Thickness (Å) | Sheet R (Ω/Sq) | Resistivity (μΩ-cm) |
|---|---|---|
| 379.7 | 10.52 | 39.9 |
| 197.7 | 19.99 | 39.5 |
| 380.6 | 10.94 | 41.6 |
| 422.7 | 9.95 | 42.1 |
| 122.9 | 30.56 | 37.6 |

The sheet resistance of cobalt films thicker than 197.7 Å was less than 20Ω/Sq, and the resistivity in all cases was less than 45 μΩ-cm.

Next, the flow rate of CCTBA precursor was reduced to 50 μmoles/minute. The sheet resistance and resistivity values of the corresponding cobalt films are set out in Table 8 below.

TABLE 8

| XRF Thickness (Å) | Sheet R (Ω/Sq) | Resistivity (μΩ-cm) |
|---|---|---|
| 287.9 | 13.67 | 39.4 |
| 118.3 | 30.53 | 36.1 |
| 282.8 | 13.93 | 39.4 |
| 323.7 | 12.28 | 39.8 |
| 74 | 42.11 | 31.2 |

The resistivity of the cobalt films at such reduced flow rate of 50 μmoles/minute was less than 40 μΩ-cm in all cases, with both thick and thin films.

Figure 13:
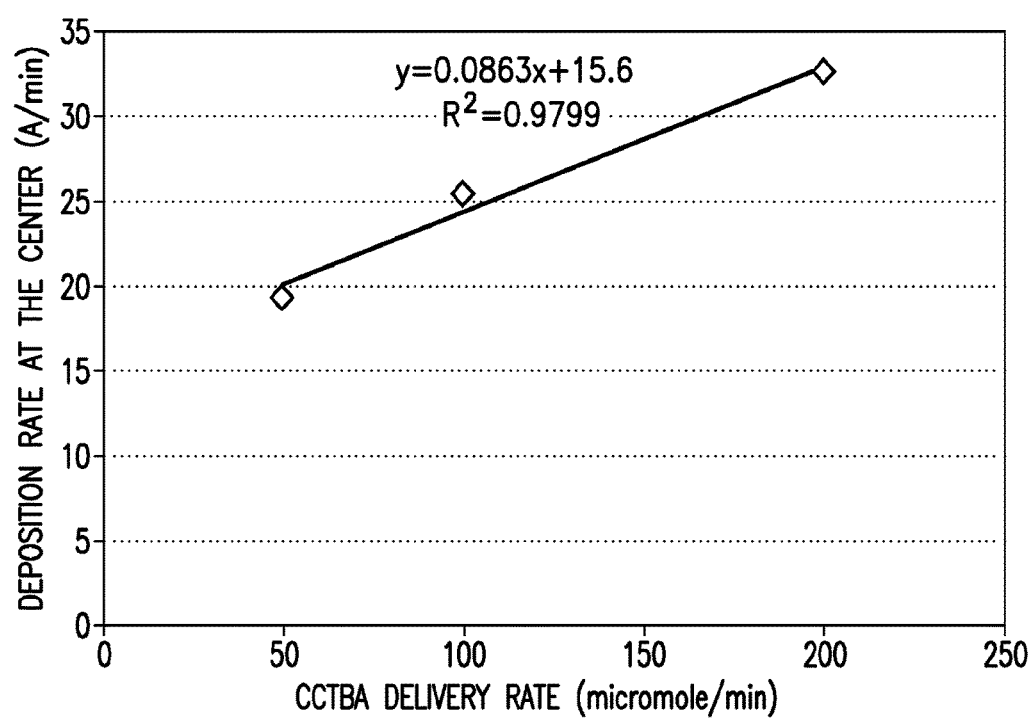
FIG. 13 is a graph of deposition rate, as determined at the center of the substrate, in Angstroms/minute, as a function of CCTBA delivery rate, in micromoles per minute, showing a linear relationship between deposition rate and precursor delivery rate, with deposition rate increasing over the CCTBA delivery rate range of from 50 to 200 μmoles per minute.
Figure 14:
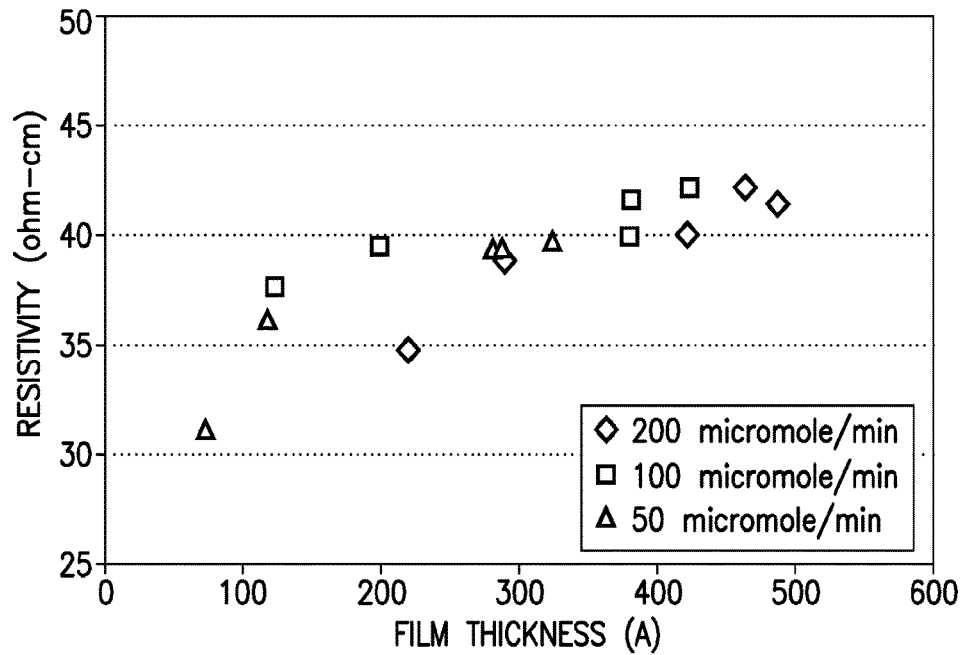
FIG. 14 is a graph of resistivity, in ohm-centimeters, as a function of film thickness, in Angstroms, for cobalt films at film thicknesses over a range of 75 to 500 Å.

The effects of precursor delivery rate are shown in FIGS. 13 and 14. FIG. 13 is a graph of deposition rate, as determined at the center of the substrate, in Angstroms/minute, as a function of CCTBA delivery rate, in micromoles per minute. FIG. 14 is a graph of resistivity, in ohm-centimeters, as a function of film thickness, in Angstroms.

FIG. 13 shows a linear relationship between deposition rate and precursor delivery rate, with deposition rate increasing over the CCTBA delivery rate range of from 50 to 200 μmoles per minute. FIG. 14 shows the resistivity of cobalt films at film thicknesses over the range of 75 to 500 Å being below 45 μΩ-cm at all precursor delivery rates over the range of from 50 to 200 μmoles per minute.

The effects of deposition time on film thickness and resistivity are shown in FIGS. 15 and 16, for deposition of cobalt films at a precursor delivery rate of 100 μmoles/minute.

FIG. 15 is a graph of film thickness, in Angstroms, as a function of deposition time, in minutes, showing the linear relationship between such variables.

FIG. 16 is a graph of resistivity, in μΩ-cm, as a function of film thickness, in Angstroms, for cobalt films deposited at a delivery rate of 100 μmoles/minute, at deposition times of 5 minutes, 10 minutes, and 15 minutes. The resistivity values determined in these tests were generally below 50 μΩ-cm.

The effects of temperature, pressure, and post-deposition rapid thermal anneal (RTN) were evaluated. Baseline deposition conditions included a concentration of CCTBA of 0.1 M in octane, delivery of the precursor at 0.1 cc/minute, with the substrate heater at temperature of 155° C., and the chamber body at 70° C., a chamber pressure of 10 torr, vaporizer temperature of 70° C., a helium carrier gas flow rate of 100 sccm, a hydrogen co-reactant flow rate of 1 liter per minute (lpm), and a deposition period of 15 minutes. The results are shown in Table 5 below.

The effects of pressure are shown in FIGS. 17 and 18. FIG. 17 is a graph of resistivity, in μΩ-cm, as a function of film thickness, in Angstroms, for cobalt films deposited from CCTBA at a delivery rate of 100 μmoles/minute, and a deposition time of 15 minutes, at pressures of 2, 5, and 10 torr. FIG. 18 is a graph of deposition rate, in Angstroms per minute, as a function of deposition pressure, in torr, for cobalt films deposited from CCTBA at a delivery rate of 100 μmoles/minute, and a temperature 150° C.

The data shown in FIGS. 17 and 18 show that reducing pressure decreases deposition rate, and improves uniformity, but increases film resistivity.

Effects of temperature are shown in FIGS. 19 and 20. FIG. 19 is a graph of resistivity, in μΩ-cm, as a function of film thickness, in Angstroms, for cobalt films deposited from CCTBA at a delivery rate of 100 μmoles/minute, and a deposition time of 15 minutes, at temperatures of 120° C., 130° C., 140° C., 150° C., and 160° C. FIG. 20 is a graph of deposition rate, in Angstroms per minute, as a function of deposition temperature, in degrees Centigrade, for cobalt films deposited from CCTBA at a delivery rate of 100 μmoles/minute, and a pressure of 10 torr.

The data shown in FIGS. 19 and 20 indicates the uniformity improves with lower deposition temperature, with lowest resistivity being achieved at 130° C.

The effects of deposition chamber temperature are shown in Table 9, for deposition of cobalt from CCTBA precursor vapor at precursor temperature of 150° C. and a pressure of 10 torr in the deposition chamber.

TABLE 9

| Chamber Temp (C.) | XRF Thickness (Å) | Sheet Resistance (ohm/sq) | Resistivity (ohm-cm) |
|---|---|---|---|
| 70 | 379.7 | 10.52 | 39.9 |
| 70 | 422.7 | 9.95 | 42.1 |
| 70 | 380.6 | 10.94 | 41.6 |
| 70 | 197.7 | 19.99 | 39.5 |
| 70 | 122.9 | 30.56 | 37.6 |
| 50 | 354.1 | 9.859 | 34.9 |
| 50 | 390.5 | 9.092 | 35.5 |
| 50 | 314.6 | 10.73 | 33.8 |
| 50 | 140.4 | 22.01 | 30.9 |
| 50 | 104 | 26.75 | 27.8 |

The data in Table 9 shows that reducing the vaporizer/chamber temperature from 70° C. to 50° C. reduced the film resistivity.

The effects of 400° C. RTN treatment of the cobalt films deposited from CCTBA were determined, with the data set out in Table 10 below.

TABLE 10

| XRF Thickness (Å) | As-dep Sheet Resistance (ohm/Sg) | As-dep Resistivity (μohm-cm) | 400 C. RTN Sheet R (ohm/Sq) | Calculated RTN Resistivity (μohm-cm) |
|---|---|---|---|---|
| 156.9 | 25.27 | 39.6 | 11.31 | 17.7 |
| 199.4 | 34.85 | 69.5 | 10.39 | 20.7 |
| 103.7 | 453.1 | 469.9 | 41.06 | 42.6 |

As shown in the data of Table 10, the post-deposition RTN treatment of the cobalt films resulted in a 55 to 90% reduction in film resistivity.

The effects of precursor delivery rate was evaluated. Baseline deposition conditions included a concentration of CCTBA of 0.1 M in octane, delivery of the precursor at 0.1 cc/minute, with a substrate temperature of 150° C., and the vaporizer and chamber body at 70° C., a chamber pressure of 10 torr, a helium carrier gas flow rate of 100 sccm, a hydrogen co-reactant flow rate of 1 liter per minute (lpm), and a deposition period of 15 minutes.

FIG. 21 is a graph of resistivity, in μΩ-cm, as a function of film thickness, in Angstroms, for cobalt films deposited from CCTBA at a temperature of 150° C., pressure of 10 torr, and deposition period of 15 minutes, for precursor delivery rates of 10, 20, 50, 100, and 200 μmoles/minute. FIG. 22 is a graph of deposition rate, measured at the center of the substrate, in Angstroms per minute, as a function of CCTBA delivery rate, in μmoles/minute, at temperature of 150° C. and a pressure of 10 torr.

FIGS. 21 and 22 show that reducing precursor delivery rate reduced deposition rate and film resistivity.

Differences in cobalt film thickness measured by x-ray fluorescence (XRF) and scanning electron microscope (SEM) were analyzed for cobalt films deposited from CCTBA precursor, at the delivery rates shown in Table 11 below.

TABLE 11

| CCTBA Delivery (μmole/min) | XRF Thickness (Å) | SEM Thickness (Å) | Resistivity (μΩ-cm) | Corrected Resistivity (μΩ-cm) |
|---|---|---|---|---|
| 200 | 421.7 | 546 | 39.84 | 51.6 |
| 100 | 380.6 | 532 | 41.64 | 58.2 |
| 50 | 282.8 | 456 | 39.4 | 63.5 |
| 100 | 135* | 243 | 49.2 | 88.6 |
| 20 | 92 | 152 | 25.44 | 42.0 |
| 10 | 66.6 | 119 | 27.58 | 49.3 |
| 20 | 175.2** | 245 | 21.7 | 30.3 |

*deposition period of five minutes
**deposition period of 30 minutes

Resistivity, in μΩ-cm, as a function of SEM film thickness, in Angstroms, is shown in FIG. 23, for cobalt films deposited from CCTBA precursor vapor, at temperature of 150° C., and pressure of 10 torr, at precursor delivery rate of 10-20 μmoles/minute (■) and at precursor delivery rate of 50-200 μmoles/minute (♦).

SIMS analysis was conducted on a cobalt film formed by vapor deposition of cobalt using CCTBA as a precursor, at a precursor flow rate of 200 μmoles/minute, for which data is set out in the first row of Table 11. The film contained ~4.75 at % carbon and ~0.15 at % oxygen. The SIMS plot is shown in FIG. 24, with concentrations of Si, Co, O, C, and N being shown, in atoms/cc, as a function of depth, in nanometers.

Spectroscopic ellipsometry thickness determinations then were made, and compared with the XRF and SEM values previously determined for the cobalt film samples identified in the fifth and seventh rows of Table 11 that were deposited at a CCTBA delivery rate of 20 μmoles/minute.

The fifth row sample as shown in Table 11 had XRF thickness of 92 Å, SEM thickness of 152 Å, and this sample had an ellipsometry thickness of 119 Å, so that the corresponding resistivity values were 25.44, 42.0, and 32.9 μΩ-cm, respectively; the atomic force microscope (AFM) root mean square roughness (RMS) of such sample was 11.4 Å, with an AFM Z range of 92.6 Å.

The seventh row sample as shown in Table 11 had XRF thickness of 175.2 Å, SEM thickness of 245 Å, and this sample had an ellipsometry thickness of 72.8 Å, so that the corresponding resistivity values were 21.7, 30.3, and 30.2 μΩ-cm, respectively; the atomic force microscope (AFM) root mean square roughness (RMS) of such sample was 6.8 Å, with an AFM Z range of 56.5 Å.

Deposition rates were determined for MOCVD processes using CCTBA precursor to form cobalt films, with precursor delivery rates of 20 and 100 μmoles/minute, at a delivery temperature of 150° C. and 10 Torr pressure. The data from such determination are plotted in FIG. 25, as film thickness, in Angstroms, as a function of deposition time, in minutes, and show that the deposition rate was approximately 6 Å/minute at 150° C. and a precursor delivery rate of 20 μmoles/minute.

Temperature effects were assessed for the deposition of cobalt films from CCTBA, delivered at a precursor supply rate of 20 and 100 μmoles/minute, at pressure of 10 torr. FIG. 26 shows the resulting data, plotted as deposition rate, in Angstroms/minute, as a function of deposition temperature, in degrees Centigrade. FIG. 27 shows corresponding resistivity values, in μΩ-cm, as a function of film thickness, in Angstroms, for cobalt films formed from CCTBA at precursor delivery rate of 20 μmoles/minute, at 130° C., 150° C., 170° C., and 190° C.

Pressure effects were evaluated for deposition of cobalt films from CCTBA, delivered at a precursor supply rate of 20 μmoles/minute, for which data is shown in FIGS. 28 and 29.

FIG. 28 is a graph of deposition rate, in Angstroms/minute, as a function of deposition pressure, in Torr, showing the linear deposition rate/deposition pressure relationship at 20 μmoles/minute, and for comparison, at 100 μmoles/minute.

FIG. 29 is a graph of resistivity, in μΩ-cm, as a function of film thickness, in Angstroms, for deposition of cobalt films from CCTBA, delivered at a precursor supply rate of 20 μmoles/minute for 15 minutes, at pressures of 10, 15, 20 and 25 torr. As shown, all resistivity values were below 25 μΩ-cm. The data show that film uniformity decreases with increasing pressure.

FIG. 30 is a graph of film thickness, in Angstroms, as a function of deposition time, in minutes, for cobalt films deposited using non-purified CCTBA precursor and high purity (HP) CCTBA precursor, at a deposition temperature of 150° C., a deposition pressure of 10 torr, a precursor flow rate of 20 μmoles/minute, and a flow rate of 1 liter per minute of co-reactant hydrogen. The non-purified CCTBA precursor exhibited a linear relationship between film thickness and deposition time in accordance with the equation y=5.6495x+9.9 ($R^2$=0.9995). The high purity CCTBA precursor exhibited a linear relationship between film thickness and deposition time in accordance with the equation y=7.8794x+14.698 ($R^2$=0.9974). The measured deposition rates for the high purity CCTBA were approximately 40% higher than for the non-purified CCTBA, thereby reflecting the value of maximizing the purity of the cobalt precursor that is used to deposit cobalt.

Cobalt deposition in accordance with the present disclosure is usefully employed in the fabrication of various products, including semiconductor devices, flat-panel displays, and solar panels. In such applications, cobalt deposited in accordance with the present disclosure is usefully employed as a substitute for copper and tungsten metal layers.

Cobalt deposition in accordance with the present disclosure is usefully employed for selective metallization of cobalt on a metal, e.g., copper, tungsten, nickel, aluminum, titanium, molybdenum, chromium, iron, manganese, zirconium, beryllium, aluminum, yttrium, and hafnium, as well as other metals, and metal alloys, metal nitrides, and metal oxides of one or more of the foregoing metals. Cobalt deposition in accordance with the present disclosure may also be employed for selective metallization of cobalt on dielectric (including high k as well as low k) materials, such as oxides of zirconium, beryllium, aluminum, silicon, yttrium, hafnium, etc., and other dielectric materials. Cobalt deposition in accordance with the present disclosure may also be employed for selective metallization of cobalt on barrier materials. Considering metals and oxide materials more generally, CCTBA may be preferred in various applications as a metallization precursor for depositing cobalt on metals, while CCTMSA and CCBTMSA may be preferred in specific applications as metallization precursors for depositing cobalt on oxide materials.

In specific applications, cobalt deposited utilizing the cobalt precursors of the present disclosure may be utilized as an electrode, such as with a high k gate or capacitor structure, as a capping layer, e.g., over a copper structure or via, and/or as an encapsulating layer, such as for covering all sides of a copper interconnect element, in a specific product device or intermediate structure for such device. Additionally, cobalt deposited in accordance with the present disclosure can be utilized as a diffusion barrier material, as well as for forming a "seed" layer for subsequent electroplating of metal thereon. The disclosure therefore contemplates corresponding articles comprising high purity, low resistivity cobalt deposited on a substrate, as formed by a method comprising a process of the present disclosure.

While the disclosure has been set forth herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the disclosure as hereinafter claimed is intended to be broadly construed and interpreted, as including all such variations, modifications and alternative embodiments, within its spirit and scope.

What is claimed is:

1. A cobalt deposition process, comprising:
   volatilizing a cobalt precursor selected from among CCTMSA, and CCBTMSA, to form a precursor vapor; and
   contacting the precursor vapor with a substrate under vapor deposition conditions effective for depositing on the substrate (i) high purity, low resistivity cobalt or (ii) cobalt that is annealable by thermal annealing to form high purity, low resistivity cobalt.

2. The process of claim 1, wherein:
   the deposited cobalt forms an electrode, or
   the deposited cobalt forms an electrode and the substrate comprises a high k gate or capacitor structure; or
   the deposited cobalt forms a capping layer, or
   the deposited cobalt forms a capping layer and the capping layer overlies a copper structure or via, or
   the deposited cobalt forms an encapsulating layer, or
   the deposited cobalt forms an encapsulating layer and the encapsulating layer covers a copper interconnect element, or
   the deposited cobalt forms a diffusion barrier, or
   deposited cobalt forms a seed for electroplating of metal thereon.

3. The process of claim 1, wherein said vapor deposition conditions comprise a deposition temperature in a range of from 25° C. to 400° C.

4. The process of claim 1, wherein the cobalt precursor is volatilized by vaporization of a solvent solution thereof, the solvent solution comprising organic solvent.

5. The process of claim 4, wherein the solvent comprises octane.

6. The process of claim 1, wherein the precursor vapor is transported in a carrier gas for the contacting thereof with the substrate, the carrier gas comprising gas selected from the group consisting of argon, neon, xenon, krypton, helium, and hydrogen.

7. The process of claim 1, wherein the cobalt precursor comprises CCTMSA.

8. The process of claim 1, wherein the cobalt after being deposited on the substrate is annealed by thermal annealing.

9. The process of claim 8, wherein the thermal annealing is conducted at temperature in a range of from 200° C. to 600° C.

10. The process of claim 8, wherein the thermal annealing is conducted for a period of time sufficient to reduce resistivity of the deposited cobalt, by an amount in a range of from 25% to 90% of the as-deposited resistivity of the cobalt film.

11. The process of claim 1, wherein said contacting of the precursor vapor with the substrate is carried out for a period of time sufficient to deposit cobalt on the substrate at a thickness in a range of from 2 nm to 1000 nm.

12. The process of claim 1, wherein the cobalt deposited on the substrate has a resistivity in a range of from 2 to 48 $\mu\Omega$-cm.

13. The process of claim 1, wherein the cobalt deposited on the substrate has a resistivity in a range of from 10 to 40 $\mu\Omega$-cm.

14. The process of claim 1, wherein the cobalt deposited on the substrate has a current density in a range of from $10^{-1}$ to $10^{-6}$ Amperes/cm$^2$ at an applied voltage of 0.5V.

* * * * *